US009333291B2

(12) United States Patent
Jacobson et al.

(10) Patent No.: US 9,333,291 B2
(45) Date of Patent: May 10, 2016

(54) INFUSION PUMP BATTERY CAPACITY MANAGEMENT AND BATTERY CHARGE ALERT SYSTEM AND METHOD

(71) Applicants: James D. Jacobson, Lindenhurst, IL (US); Tadas S. Sileika, Northbrook, IL (US); William K. Day, Hoffman Estates, IL (US)

(72) Inventors: James D. Jacobson, Lindenhurst, IL (US); Tadas S. Sileika, Northbrook, IL (US); William K. Day, Hoffman Estates, IL (US)

(73) Assignee: Hospira, Inc., Lake Forest, IL (US)

( * ) Notice: Subject to any disclaimer, the term of this patent is extended or adjusted under 35 U.S.C. 154(b) by 0 days.

(21) Appl. No.: 14/598,846

(22) Filed: Jan. 16, 2015

(65) Prior Publication Data
US 2015/0196709 A1   Jul. 16, 2015

Related U.S. Application Data

(60) Provisional application No. 62/089,691, filed on Dec. 9, 2014, provisional application No. 61/928,305, filed on Jan. 16, 2014.

(51) Int. Cl.
*H02J 7/00* (2006.01)
*A61M 5/142* (2006.01)

(52) U.S. Cl.
CPC ............ *A61M 5/14244* (2013.01); *A61M 5/142* (2013.01); *A61M 5/14228* (2013.01); *A61M 2005/14208* (2013.01); *A61M 2205/18* (2013.01); *A61M 2205/332* (2013.01);

(Continued)

(58) Field of Classification Search
CPC ............... A61M 2005/14208; A61M 2205/50; A61M 2205/8206; A61M 2205/8212
USPC .............................. 320/107, 132, 134; 604/67
See application file for complete search history.

(56) References Cited

U.S. PATENT DOCUMENTS

| 4,692,145 A | 9/1987 | Weyant |
| 5,321,392 A | 6/1994 | Skakoon et al. |

(Continued)

FOREIGN PATENT DOCUMENTS

WO    2011109774 A1    9/2011

OTHER PUBLICATIONS

Hospira, Inc., Hospira Plum XL Series Infusion Systems (Service Manual), Feb. 2005, pp. i-vii, 5-14, 8-3, Lake Forest, Illinois, USA.

*Primary Examiner* — Edward Tso
*Assistant Examiner* — Aaron Piggush
(74) *Attorney, Agent, or Firm* — Michael R. Crabb

(57) ABSTRACT

Enables an infusion pump battery capacity management and battery charge alert system and method including an infusion pump with rechargeable batteries, a controller, a computer and a user interface. The infusion pump accepts a programmed infusion and selects a battery capacity assessment option to determine one or more recharge options of the batteries, and may optionally select a program delay option to execute an infusion delay and later select the battery capacity assessment option. During the battery capacity assessment option, the infusion pump calculates an anticipated power capacity requirement to execute the programmed infusion, calculates a remaining battery power capacity, compares the calculated anticipated power capacity requirement to the calculated remaining battery power capacity, and determines whether the infusion pump is able to fully execute the programmed infusion based only on the remaining battery power capacity or whether a recharge is required.

15 Claims, 15 Drawing Sheets

(52) U.S. Cl.
CPC ...... *A61M2205/50* (2013.01); *A61M 2205/502* (2013.01); *A61M 2205/505* (2013.01); *A61M 2205/52* (2013.01); *A61M 2205/8206* (2013.01); *A61M 2205/8212* (2013.01); *A61M 2205/8237* (2013.01); *H02J 7/00* (2013.01)

(56) References Cited

U.S. PATENT DOCUMENTS

| | | |
|---|---|---|
| 5,712,795 A | 1/1998 | Layman et al. |
| 5,764,034 A | 6/1998 | Bowman et al. |
| 5,814,015 A | 9/1998 | Gargano et al. |
| 5,882,300 A | 3/1999 | Malinouskas et al. |
| 5,973,497 A | 10/1999 | Bergk et al. |
| 6,236,326 B1 | 5/2001 | Murphy et al. |
| 7,430,675 B2 | 9/2008 | Lee et al. |
| 8,287,514 B2 | 10/2012 | Miller et al. |
| 8,622,990 B2 | 1/2014 | Estes et al. |
| 8,665,214 B2 | 3/2014 | Forutanpour et al. |
| 8,706,233 B2 | 4/2014 | Su et al. |
| 8,792,981 B2 | 7/2014 | Yudovsky et al. |
| 8,823,382 B2 * | 9/2014 | Rondoni ............... A61N 1/3708 320/134 |
| 2009/0209945 A1 * | 8/2009 | Lobl ................. A61M 5/14224 604/891.1 |
| 2011/0162647 A1 | 7/2011 | Huby et al. |
| 2012/0194341 A1 | 8/2012 | Peichel et al. |
| 2012/0226350 A1 | 9/2012 | Rudser et al. |

* cited by examiner

INFUSION PUMP BATTERY CAPACITY MANAGEMENT AND BATTERY CHARGE ALERT SYSTEM AND METHOD

CROSS REFERENCE TO RELATED APPLICATIONS

This application claims the benefit of U.S. Provisional Patent Application 61/928,305 filed on 16 Jan. 2014, and U.S. Provisional Patent Application 62/089,691 filed on 9 Dec. 2014, the specifications of which are hereby incorporated herein by reference.

BACKGROUND OF THE INVENTION

1. Field of the Invention

One or more embodiments of the invention are related to the field of infusion pump power management systems and battery charge alert systems. Specifically, one or more embodiments relate to a system and method of determining remaining battery capacity of an infusion pump and providing a message to a user before infusion begins, if a particular infusion will require a recharge based on the particular infusion to be performed and based on the current remaining battery capacity. At least one embodiment determines a required remaining duration of a programmed infusion of an infusion pump, an anticipated power capacity requirement to fully execute the programmed infusion, the remaining power capacity of batteries of the infusion pump, and whether the infusion pump will require a recharge prior to ambulation to avoid unexpected or premature therapy stoppage.

2. Description of the Related Art

Generally, ambulatory pumps are unique among infusion pumps in that patients on these pumps are anticipated to be somewhat mobile. In addition, ambulatory pumps, typically, may be used outside highly monitored clinical environments, such as in homes and alternate site locations. Generally, infusion systems rely on a combination of energy from main power sources and battery-powered sources to provide power for therapy delivery. Typically, during instances when power from a main power source is unavailable, such as during patient ambulation or during a grid-based power outage, the therapy delivery, such as infuser operation, is entirely dependent on a battery. These unique use cases provide challenges in managing the use of batteries incorporated within the infusion pump, as patients are typically not tethered to alternating current or "AC" power. In contrast, most hospital infusion pumps, such as syringe pumps or general IV/large volume pumps, are typically connected to AC power bedside and under most conditions remain plugged in, with exceptions being during patient transport and other short term events or lapses in plugging a pump back in following such an event. For example, hospital "pole-mounted" pumps typically use internal rechargeable batteries as a backup power source but are intended to be driven primarily by wall power. Ambulatory pumps, however, are generally used for long lengths of time, and potentially for entire infusion sessions, strictly on battery power. Ambulatory pumps have traditionally been designed around the use of disposable "drop-in" batteries, though the emergence of internal rechargeable batteries has been demonstrated in ambulatory pumps. Typically, the remaining charge within the battery ultimately determines the duration that therapy may continue without input from the main power source.

Infusion pumps are typically programmed without regard for the manner in which the pump will be powered throughout the specific infusion. For example, it may be anticipated that the pump will have sufficient power capacity available throughout AC power or internal batteries, and that overall power needs, low batteries, temporary or longer term lack of access to AC power, and other power management issues will be managed by the caregiver in a clinical environment, or by a patient or caregiver in a home or alternate site setting. In home infusion, a typical solution to ensure that sufficient battery life is available to complete an infusion, requires that new drop-in batteries are installed for each infusion, or every two infusions, per known battery capacities, therapy profiles, and intuition developed by the home infusion company over time. This has proven to be an expensive solution that leads to inefficient use of batteries since they are generally disposed of even when they still have remaining battery capacity. Also there is no link demonstrated between battery capacity and the required capacity to complete the programmed infusion.

The use of internal rechargeable batteries, generally, provides a solution to the economic challenges and practical implementation challenges of this previous practice, including the extreme case of trips to homes of patients to deliver new batteries. Introduction of a rechargeable battery into this use case introduces new practical challenges in that batteries may have unknown capacity prior to use, versus new "full" alkaline batteries, and that the ability to easily replace internal batteries may not be an option to the patient or caregiver. However, migration of the industry towards internal rechargeable batteries is inevitable, following the course of mobile electronic devices, such as laptop computers and cellular phones and the aforementioned benefits in total cost of use.

Generally, hospital infusion pumps utilize rechargeable internal batteries as backup batteries. These products all typically share details on battery capacity via % of remaining capacity, and often offer remaining battery capacity in only discrete values such as 25%, 50%, 75%, etc. Ambulatory pumps have been introduced that utilize disposable batteries as well as internal rechargeable batteries. These products also typically share details on battery capacity via % of remaining capacity. However, typical solutions generally do not relate remaining capacity to remaining infusion time. For example, remaining capacity is communicated only as a percentage of remaining charge and no translation of this metric to the remaining infusion time is provided or suggested. (Wearable pumps, such as insulin delivery pumps, are considered as a different category from ambulatory pumps as defined here and typically utilize disposable batteries and operate more or less continuously for the Type 1 diabetic patient.) Significant disadvantages of typical methods of communicating remaining battery capacity to users are that ambulatory pump users in a home may not be experienced and may not have yet have developed sophisticated intuition around remaining battery capacity and its link to remaining infusion time, which is typically dependent on infusion profile (rate and time) as well pump configurations (such as backlight or wireless communications settings). Known pumps will message or alarm "low battery" when operating on battery power and available battery capacity drops below a (often configurable) remaining infusion time, such as 30 minutes. However, such an alarm or message presents no forewarning and as such can leave the user in a position where they are unable to either change disposable batteries or access AC or other power sources to recharge internal batteries, a significant limitation to the ambulatory patient.

Generally, when the main power is lost or when a patient ambulates along with an infuser, the clinician may inquire only in a generally manner about the remaining battery charge. This is accomplished by observing an on-screen icon or another visual indicator, that typically displays an estimated fraction of the remaining battery capacity in a non-numeric graphical icon format. Nurses have generally reported that by not checking the battery charge remaining prior to ambulation has often resulted in stopping of therapy en route, as the required power consumption depletes the battery.

For example, U.S. Pat. No. 5,712,795 to Layman et al., entitled "Power Management System" discloses a power management system that appears to manage the power to operate a medical device internal battery to ensure the battery remains at full charge. The power management system of Layman et al., for example, may monitor the capacity of the battery and calculate the remaining charge of the battery based on charging activities and usage, and therefrom calculates the battery run time. However, the system appears to lack any teaching or suggestion of an infusion pump battery capacity management system that provides a notification or a warning to a user before infusion begins, that a particular infusion will require a recharge before or during therapy based on the current battery capacity. This system, as well as each of the other systems listed below, appears to lack any teaching or suggestion of an infusion pump battery capacity management system that provides a notification or a warning to a user during an infusion or following a change to the infusion that completion of the infusion will require a recharge.

U.S. Pat. No. 8,287,514 to Miller et al. entitled "Power Management Techniques For An Infusion Pump System" discloses various power management techniques that may avoid substantial power usage during operation of a pump system. The system of Miller et al. appears to use a pump system that may draw on energy supply to extend the life of the power supply and estimate the amount of power remaining to operate the pump system. However, the system appears to lack any teaching or suggestion of an infusion pump battery capacity management system that provides a notification or a warning to a user before infusion begins, that a particular infusion will require a recharge at some point based on the current battery capacity.

United States Patent Publication 20110162647 to Huby et al. entitled "Power Management In Respiratory Treatment Apparatus" discloses a respiratory apparatus that may provide treatment with a power management control, providing efficient power consumption to control the operations of various elements within the respiratory apparatus. For example, the system may control one or more elements of the apparatus to permit flow during peak power operation to minimize power drain of the power supply. In addition, the system appears to suggest estimating power needed for a typical sleep session for example based on stored historic treatment session information previously recorded. However, the system appears to lack any teaching or suggestion of an infusion pump battery capacity management system that provides a notification or a warning to a user before infusion begins, that a particular infusion will require a recharge based on the current battery capacity.

U.S. Pat. No. 5,814,015 to Gargano et al., entitled "Infusion Pump for at Least One Syringe", discloses a processor driven syringe pump that operates in a rate, volume or amount per time, or pharmacokinetic mode by accepting input selections for a regimen and displaying operating conditions. The system of Gargano et al. appears to disclose a software program that provides a number of feedback warnings and alarms including battery status, remaining infusion time, etc. According to Gargano et al., the software also provides a continuous indication of remaining battery life on a display. However, the system of Gargano et al. appears to lack any teaching or suggestion of a battery charge alert system that provides a notification, alert or a warning to a user before infusion begins, of how long an active therapy will last on the battery power alone, for example during patient ambulation. In addition, the system of Gargano et al. appears to lack any teaching or suggestion of mitigating unexpected or premature stopping of therapy by a medical device when operating on battery power alone, for example through detection of potential ambulation events.

For example, U.S. Pat. No. 5,764,034 to Bowman et al. entitled "Battery Gauge For A Battery Operated Infusion Pump" discloses a system that may estimate the amount of time left on a battery by monitoring the voltage available and current flowing from the battery, and the amount of current flowing from the battery, to provide accurate battery monitoring during an ambulatory session for example. The system of Bowman et al. appears to disclose wherein the use of the auxiliary battery power raises the issue of monitoring of the available power in the battery at any given time. In addition, the system appears to provide a warning when battery voltage has decreased below a predetermined value. However, the system of Bowman et al. appears to lack any teaching or suggestion of mitigating unexpected or premature stopping of therapy by a medical device when operating on battery power alone, for example through detection of potential ambulation events. Furthermore, the system appears to lack any teaching or suggestion of an infusion pump battery capacity management system that provides a notification or a warning to a user before infusion begins, that a particular infusion will require a recharge at some point during the infusion based on the current battery capacity.

U.S. Pat. No. 5,321,392 to Skakoon et al. entitled "Infusion Pump With Battery Back-Up" discloses an infusion pump that may be powered via an AC line or via a battery, wherein a notification is provided when the pump detects that the battery has been depleted. However, the system appears to lack any teaching or suggestion of an infusion pump battery capacity management system that provides a notification or a warning to a user before infusion begins, that a particular infusion will require a recharge based on the current battery capacity.

For example, United States Patent Publication 20120226350 to Rudser et al. entitled "Controller and Power Source for Implantable Blood Pump" discloses a system for controlling the operation and power consumption of an implantable device, such that program information and modes of operation may be stored. For example, the system of Rudser et al. may generate a signal of the time remaining for operation under a current battery power, wherein such a time remaining may be displayed on a display device, such that when the time-remaining value reaches a threshold or range of values that may be dangerous to a patient, a warning is issued. However, the system appears to lack any teaching or suggestion of an infusion pump battery capacity management system that provides a notification or a warning to a user before infusion begins, that a particular infusion will require a recharge based on the current battery capacity.

World Intellectual Property Organization Publication 2011109774 to Bachman et al. entitled "Portable Controller With Integral Power Source For Mechanical Circulation Support Systems" discloses an external circulation support system with batteries and control electronics, such that the control and power sources may accommodate different patient configurations. The system of Bachman et al. appears to calculate time remaining on the power sources and track and store power drawn by components of the pump. However, the system appears to lack any teaching or suggestion of an infusion pump battery capacity management system that provides a notification or a warning to a user before infusion begins, that a particular infusion will require a recharge based on the current battery capacity.

U.S. Pat. No. 5,882,300 to Malinouskas et al., entitled "Wireless Patient Monitoring Apparatus Using Inductive Coupling", discloses a wireless apparatus wherein a transducer detects a physiological function and provides an output signal thereof. According to the system of Malinouskas et al., battery current is sensed via a voltage divider for input to a battery monitoring circuit or gauge that keeps track of battery usage and charge currents. Compensation is made for diminished battery capacity due to age and self-discharge. In embodiments of the system of Malinouskas et al., LED indicators are illuminated for a brief time period after each detected motion, at the end of battery life, and when the transducer is placed into the charging station. Furthermore, according to Malinouskas et al., when the battery is near the end of its useful charge, at least one of the LED indicators will flash and a signal is transmitted to the fetal monitor console to notify the operator. However, the system of Malinouskas et al. appears to lack any teaching or suggestion of a battery charge alert system that provides a notification, alert or a warning to a user before infusion begins, of how long an active therapy will last on the battery power alone, for example during patient ambulation. In addition, the system of Malinouskas et al. appears to lack any teaching or suggestion of mitigating unexpected or premature stopping of therapy by a medical device when operating on battery power alone, for example through detection of potential ambulation events.

U.S. Pat. No. 8,792,981 to Yudovsky et al., entitled "Omni-directional Accelerometer Device and Medical Device Incorporating Same", discloses a portable medical device with an internal accelerometer that is configured to initiate acceleration-dependent operation of the portable medical device in response to generated signals present at the sensor signals. The system of Yudovsky et al. appears to disclose an alert module that detects alert conditions, alarm conditions, notification conditions, reminder conditions, and/or other conditions that trigger or otherwise prompt the medical device to generate corresponding alerts, alarms, notifications, reminders, flags, or the like. In embodiments of the device of Yudovsky et al., the conditions detected by the alert module may be associated with the operation, status, state, functionality, or characteristics of the medical device. According to Yudovsky et al., the alert module may cooperate with the accelerometer device, an accelerometer signal processing module, and an accelerometer response module to respond to detected physical activity and/or detected physical impacts. However, the system of Yudovsky et al. appears to lack any teaching or suggestion of a battery charge alert system that provides a notification, alert or a warning to a user before infusion begins, of how long an active therapy will last on the battery power alone, for example during patient ambulation.

For example, United States Publication 20120194341 to Peichel et al., entitled "Accelerometer Feedback Control Loop for Patient Alert", discloses a system and method for delivering an alert signal to cause motion within a patient's body in response to detecting a condition. The system of Peichel et al. appears to disclose an accelerometer positioned to be sensitive to motion caused by delivering stimulation pulses to muscle tissue, wherein the accelerometer signal is received by a signal processing module and used by a controller in controlling an alert signal delivered to the patient in a closed-loop feedback method. According to Peichel et al., when an alert condition is detected, the system controls a patent alert signal using an accelerometer feedback signal, wherein such an alert may include expected battery life, battery replacement required, etc. However, the system of Peichel et al. appears to lack any teaching or suggestion of a battery charge alert system that provides a notification, alert or a warning to a user before infusion begins, of how long an active therapy will last on the battery power alone, for example during patient ambulation.

In summary, known system generally include calculating remaining battery life for a medical device, displaying warnings when the battery capacity is below a threshold and predicting remaining power. There are no known infusion pump battery management systems that provide a warning to a user before infusion begins, that a particular infusion will require a recharge, and pre-warn a user that a charge will be required based on a particular infusion to be performed and based on the current battery power level. In addition, there are no known systems that provide a user with options on proceeding with an infusion that enables the user to plan for recharging instead of reacting to a recharge warning or missing the warning altogether if they are unable to plan for a recharge. If a user falls asleep or is otherwise unconscious when a battery warning occurs, this may lead to deterioration in the user's medical condition. For at least the limitations described above there is a need for infusion pump battery capacity management system and method. In addition, in view of the above, there is a need for a system that alerts the nurse of remaining battery charge immediately prior to ambulation, via a vibratory, visual and/or audible alert. Additionally, there is a need for a system that provides estimates of the expected time duration that an active therapy will last on battery power alone, offering further insight into whether patient ambulation may be achieved without interrupting the infusion or therapy, to enable mitigating unexpected or premature stopping of therapy by a medical device when operating on battery power alone.

BRIEF SUMMARY OF THE INVENTION

The following presents a simplified summary of the present disclosure in order to provide a basic understanding of some aspects of the disclosure. This summary is not an extensive overview of the disclosure. It is not intended to identify key or critical elements of the disclosure or to delineate the scope of the disclosure. The following summary merely presents some concepts of the disclosure in a simplified form as a prelude to the more detailed description provided below.

One or more embodiments of the invention include an infusion pump battery capacity management system and battery charge alert system. In at least one embodiment, the infusion pump battery capacity management and battery charge alert system includes an infusion pump that infuses fluids that may include drugs, nutrients, blood or other liquids into a patient. In at least one embodiment, the infusion pump may include one or more rechargeable batteries, a user interface and a user interface screen, an infusion pump controller, and at least one detector that detects ambulation of the patient. In one or more embodiments, the infusion pump controller includes a computer and is directly or indirectly coupled with the user interface, or the user interface screen, or both.

By way of at least one embodiment of the invention, the infusion pump may accept an infusion input, wherein the infusion input includes a programmed infusion that may be input by one or more users via the infusion pump user interface. In one or more embodiments, the user interface may for example display, such as on the user interface screen, a start screen with a confirmation of the programmed infusion, a battery capacity assessment option, a battery charge indicator, a program delay option, a start option, and requirements of the programmed infusion, or any combination thereof. In at least one embodiment of the invention, the battery charge indicator may indicate remaining power capacity of the one or more rechargeable batteries as at least one of a percentage, a time including hours and minutes, or both the percentage and time. In at least one embodiment, the infusion pump controller may accept a selection input to select one or more of the battery capacity assessment options, the program delay option, the battery charge indicator, the requirements of the programmed infusion, and the start option, and assert a respective option.

In one or more embodiments, if the infusion pump controller asserts the start option, the programmed infusion may be executed via the infusion pump. If the infusion pump controller asserts the delay option, in embodiments of the invention, an infusion delay may be programmed and the infusion pump controller may then select the battery capacity assessment option or select the start option. If the infusion pump controller selects the battery capacity assessment option, in one or more embodiments, the infusion pump controller may calculate an anticipated power capacity requirement to execute the programmed infusion, calculate a remaining power capacity of the one or more rechargeable batteries, compare the calculated anticipated power capacity requirement to the calculated remaining power capacity of the rechargeable batteries, and determine whether the infusion pump is able to fully execute the programmed infusion based only on the remaining power capacity. In at least one embodiment of the invention, calculating an anticipated power capacity requirement to execute the programmed infusion may be based on a flow rate. Other inputs to an anticipated power capacity requirement could include infusion type (Continuous, Intermittent, etc.), volume to be infused, time of infusion, type of solution being infused, and pump configuration settings such as backlight settings or wireless communication capabilities. Other inputs to could be patient or therapy specific, extrapolating for examples high levels of user interface engagement previously in the infusion to modify expected capacity requirements.

By way of one or more embodiments, if the infusion pump controller determines wherein the infusion pump may, or is able to, fully execute the programmed infusion, such as with the required remaining duration of the programmed infusion, using only the remaining power capacity, then the infusion pump controller may assert the start option and the programmed infusion may be executed via the infusion pump, for example only using the remaining power capacity.

If the infusion pump controller determines wherein the infusion pump may be unable to fully execute the programmed infusion only using the remaining power capacity, in one or more embodiments of the invention, the infusion pump controller may assert the start option and the programmed infusion may be executed via the infusion pump, and may provide a warning, such as a message, to the user that a recharge time may be required to fully execute the programmed infusion. Since this occurs before the start of the infusion, the user may plan for the recharge, for example by setting an alarm on the pump or through an external device or alerting another user to ensure that the recharge event occurs. In this manner, embodiments of the invention enable a user to pre-plan for a recharge instead of reacting to a warning that they may not be able to hear or be awake for depending on the timing of the warning, or may not be able to respond to, for example when driving a car.

In at least one embodiment of the invention, when the infusion pump controller determines wherein the infusion pump may be able to fully execute the programmed infusion only using the remaining power capacity, the infusion pump controller may display the remaining power capacity that is sufficient to execute the programmed infusion on the user interface screen.

In one or more embodiments, the warning may be displayed as a notification on the interface screen. The notification, in embodiments of the invention, may include wherein the remaining power capacity is insufficient to execute the programmed infusion, wherein a recharge time is required during execution of the programmed infusion, and a determination of a time before the one or more rechargeable batteries are depleted, or a determination of time before the one or more rechargeable batteries are depleted within a safety level. In at least one embodiment, the recharge time may include one or more of a partial-recharge of the one or more rechargeable batteries, or a full-recharge of the one or more rechargeable batteries.

According to at least one embodiment, when the warning is provided wherein a recharge time is required to fully execute the programmed infusion, the infusion pump may enter a first recharge state or a second recharge state. In one or more embodiments, the first recharge state may include a partial recharge of the one or more rechargeable batteries or a full recharge of the one or more rechargeable batteries, to fully execute the programmed infusion, and the second recharge state may include a full recharge of the one or more rechargeable batteries and a continuous recharge of the one or more rechargeable batteries during execution of the programmed infusion. In embodiments of the invention, the first recharge state and the second recharge state may include plugging the infusion pump into the an AC power source to partially recharge the one or more rechargeable batteries, fully recharge the one or more rechargeable batteries or continuously recharge the one or more rechargeable batteries. This enables a user to provide just enough capacity to the batteries to fulfill the energy requirements of the infusion, which may include some safety margin, while minimizing the amount of time that the infusion pump is coupled to an AC outlet or other power source for example when full recharge is not required, which is unknown in the art. For example, some embodiments may allow recharging from an automobile or airplane power outlet or any other type of recharge apparatus.

In at least one embodiment, during the first recharge state, the infusion pump controller may partially or fully recharge the one or more rechargeable batteries before execution of the programmed infusion, or partially or fully recharge the one or more rechargeable batteries during execution of the programmed infusion. During the first recharge state, in embodiments of the invention, the infusion pump controller may notify the one or more users when the remaining power capacity of the one or more batteries is sufficient to fully execute the programmed infusion. In one or more embodiments, during the first recharge state, the infusion pump may defer the partial or full recharge of the one or more rechargeable batteries via the one or more users, wherein the infusion pump may determine a time deferral value and notify the one or more users with the determined time deferral value and wherein the determined time deferral value may be a value that allows the infusion pump to remain to operate safely before requiring the partial recharge or the full recharge. The deferred recharge, in one or more embodiments, by the one or more users may occur during execution of the programmed infusion.

According to at least one embodiment, during the second recharge state, the infusion pump controller may recharge the one or more rechargeable batteries by partially or fully recharging the one or more rechargeable batteries before execution of the programmed infusion and then continuously charging the one or more rechargeable batteries during execution of the programmed infusion, or partially or fully recharging the one or more rechargeable batteries during execution of the programmed infusion and continuously charging the one or more rechargeable batteries during execution of the programmed infusion, or deferring the recharge of the one or more rechargeable batteries. In one or more embodiments, the infusion pump may determine a time deferral value and may notify the one or more users with the determined time deferral value, wherein the determined time deferral value may be a value that allows the infusion pump to remain to operate safely before requiring the partial recharge or the full recharge.

According to one or more embodiments of the invention, when the at least one detector detects patient ambulation, the infusion pump controller may calculate a required remaining duration of the programmed infusion to fully execute the programmed infusion, and display the calculated required remaining duration of the programmed infusion on the user interface screen. In at least one embodiment, the infusion pump controller may calculate an anticipated power capacity requirement to fully execute the programmed infusion, and may calculate a remaining power capacity of the one or more rechargeable batteries. In one or more embodiments, the infusion pump controller may compare the calculated anticipated power capacity requirement to the calculated remaining power capacity of the one or more rechargeable batteries, and therefrom determine whether the infusion pump is able to fully execute the programmed infusion based on a comparison of the calculated required remaining duration of the programmed infusion and the calculated remaining power capacity of the one or more rechargeable batteries.

According to one or more embodiments, if the infusion pump controller determines that the infusion pump is unable to fully execute the programmed infusion with the required remaining duration of the programmed infusion only using the remaining power capacity, then the infusion pump controller provides a warning to the one or more users indicating insufficient remaining power capacity. In at least one embodiment of the invention, when the infusion pump controller determines that the infusion pump is unable to fully execute the programmed infusion with the required remaining duration of the programmed infusion using only the remaining power capacity, the infusion pump controller may provide a warning. The warning may include one or more of: a duration of time to charge that is required of the one or more rechargeable batteries prior to starting the programmed infusion to fully execute the programmed infusion with the required remaining duration of the programmed infusion; and an anticipated time when a recharge of the one or more rechargeable batteries of the infusion pump is required during execution of the programmed infusion fully execute the programmed infusion with the required remaining duration of the programmed infusion.

In at least one embodiment, the at least one detector that detects the ambulation of the patient may include one or more of an accelerometer and a wireless network interface. By way of one or more embodiments, the at least one detector that detects the ambulation of the patient may include a sensor that detects removal of a power input from the infusion pump. In one or more embodiment, the accelerometer may be coupled with the computer such that the accelerometer detects acceleration indicative of ambulation of the patient coupled with the infusion pump. In at least one embodiment, the wireless network interface is coupled with the computer such that wireless interface detects wireless connectivity changes of the infusion pump coupled with the patient that may be indicative of patient ambulation.

According to one or more embodiments, during the programmed infusion, the at least one detector may detect ambulation based on removal of a power input from the infusion pump for less than 5 minutes, and one or more of sustained infusion pump movements for at least 10 seconds detected by the accelerometer, and infusion pump movement based on 3 events of wireless connectivity change detected by the wireless network interface. Other thresholds for these events in terms of the time duration or acceleration values or wireless connection changes are in keeping with the invention. Any combination of these sensors and values and thresholds may be utilized for any one or more embodiments of the invention.

According to at least one embodiment, the infusion pump may display on the user interface screen one or more of a time-remaining counter, in the hours and minutes, that displays the calculated required remaining duration of the programmed infusion to fully execute the programmed infusion, and a therapy-progress bar. In at least one embodiment, the therapy-progress bar may include one or more of the calculated required remaining duration of the programmed infusion to fully execute the programmed infusion, the calculated remaining power capacity of the one or more rechargeable batteries, and a bar graph displaying a moving bar indicating the progress of the programmed infusion.

In one or more embodiments of the invention, the bar graph may include one or more of a first segment displaying a first therapy option time of an infusion such as a continuous infusion time of an infusion, a second segment displaying second therapy option time of an infusion such as a keep vein open (KVO) time, and a third segment highlighted along one or more of the first segment and the second segment that indicates when the remaining power capacity of the one or more rechargeable batteries will be at zero ampere-hours or watt-hours or essentially exhausted such that even if a small capacity remains it is insufficient to operate or otherwise complete an infusion. In at least one embodiment, the continuous infusion time of an infusion and the KVO time may be displayed as a rate plot. Rather than KVO, other end of infusion options are available and may be implemented in a similar manner. For example, a "continue rate" option may be offered that maintains the current delivery rate of the programmed infusion therapy or a "stop therapy" option may be offered for example.

By way of at least one embodiment, the infusion pump controller may determine and calculate one or more changes in the required remaining duration of the programmed infusion to fully execute the programmed infusion, the anticipated power capacity requirement to execute the programmed infusion, and the remaining power capacity of the one or more rechargeable batteries. In one or more embodiments, when the infusion pump controller determines and calculates the one or more changes, the infusion pump controller may provide an alert to the one or more users with updated information based on the determined and calculated one or more changes.

The details of these and other embodiments of the disclosure are set forth in the accompanying drawings and description below. Other features and advantages of aspects of the disclosure will be apparent from the description, drawings, and claims.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

An infusion pump battery capacity management and battery charge alert system and method will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
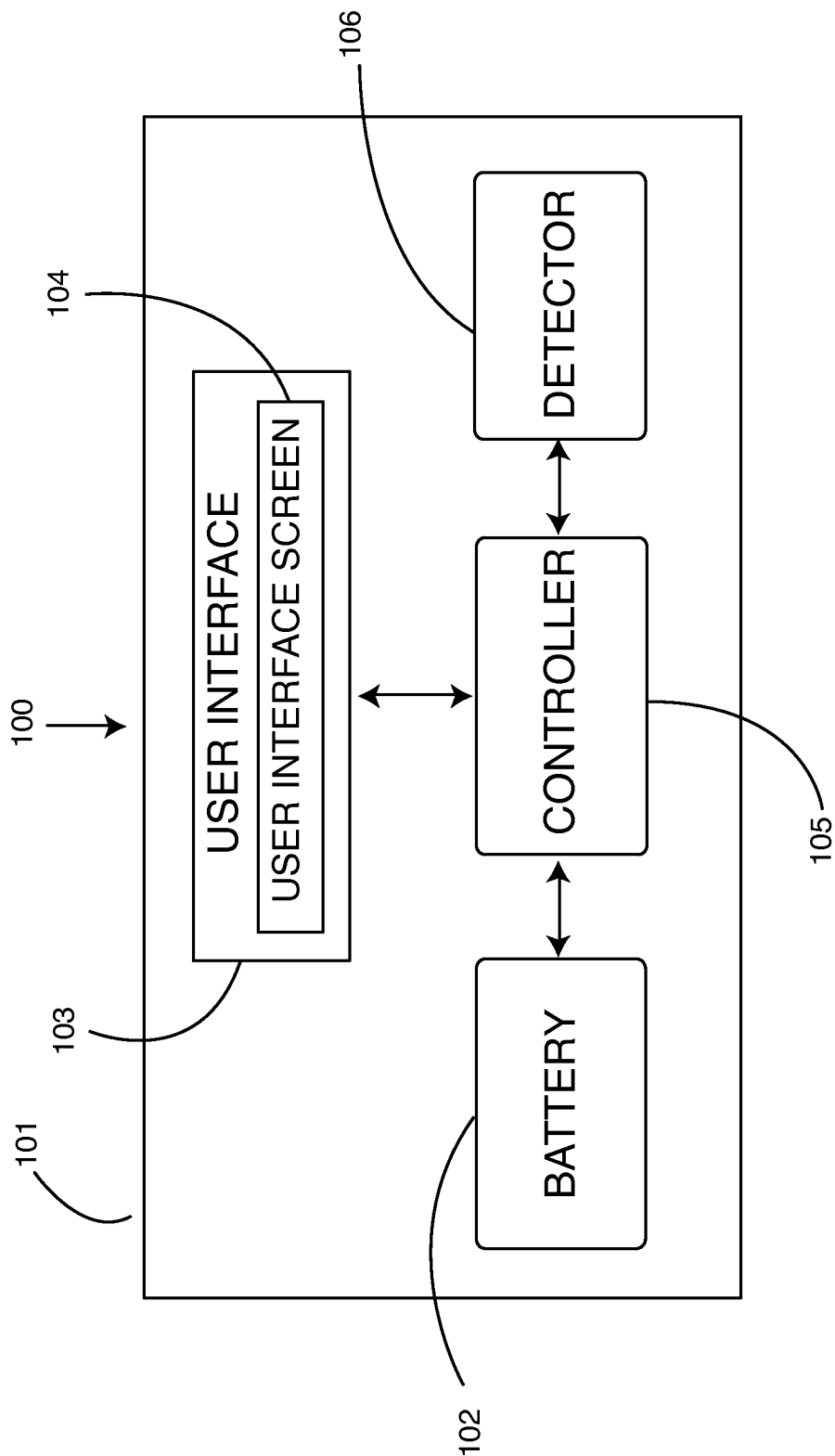
FIG. 1 shows an illustrative architecture diagram of the infusion pump battery capacity management and battery charge alert system.

FIG. 1 shows an architectural diagram of an infusion pump battery capacity management and battery charge alert system, according to one or more embodiments of the invention. As shown in FIG. 1, at least one embodiment of the invention includes an infusion pump battery charge alert system 100 including an infusion pump 101 that infuses fluids that may include drugs, nutrients, blood or other liquids into a patient. In at least one embodiment, the infusion pump 101 includes one or more rechargeable batteries 102, a user interface 103 and a user interface screen 104, an infusion pump controller 105, and at least one detector 106 that detects ambulation of the patient. In one or more embodiments, the infusion pump controller 105 includes a computer and is directly or indirectly coupled with the user interface 103 and the user interface screen 104. See also FIG. 14 for one or more embodiments of the architecture.

Figure 1A:
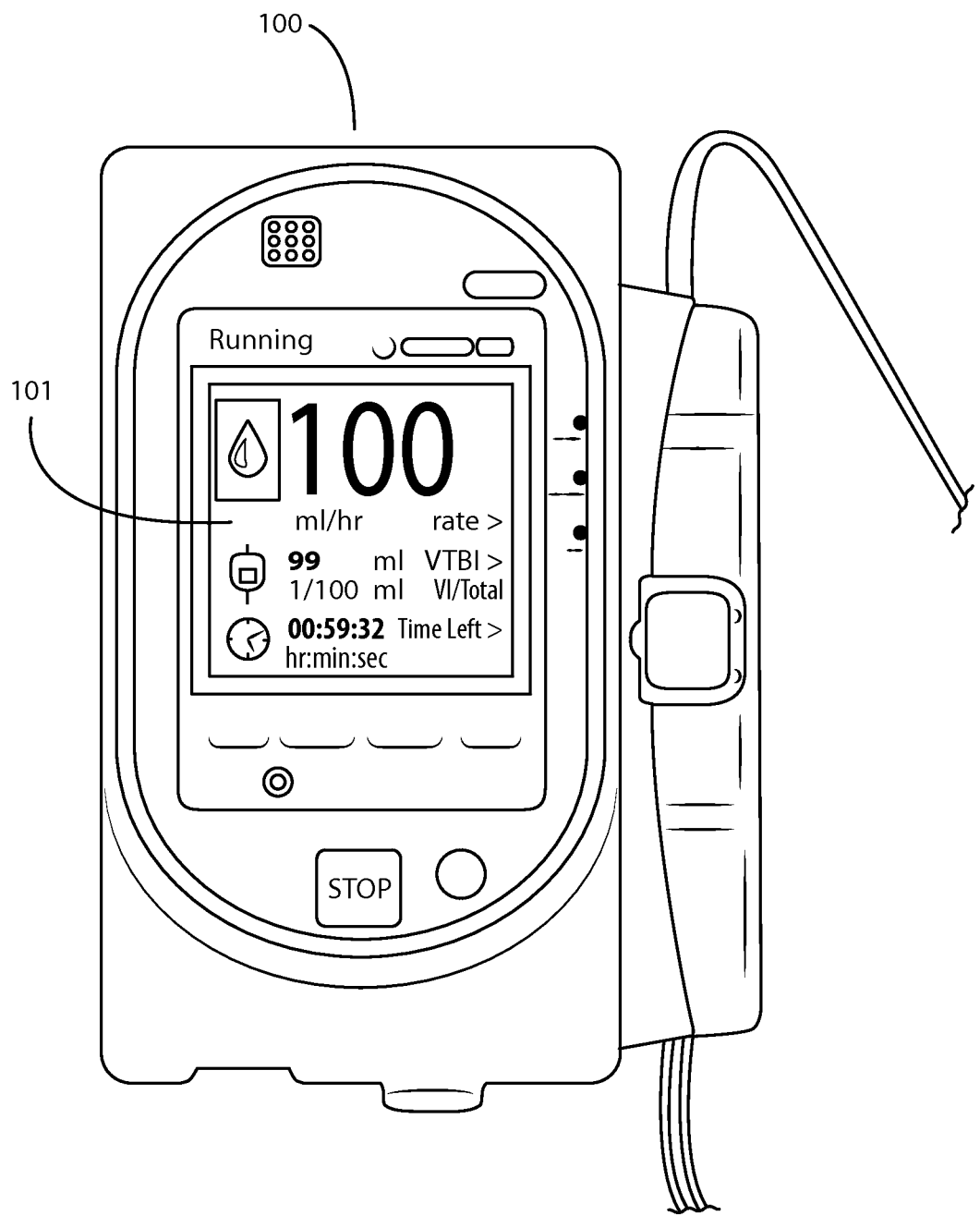
FIG. 1A illustrates a front view of one or more embodiments of an ambulatory pump, such as would be a target application of the invention.

FIG. 1A illustrates a perspective view of one or more embodiments of the invention. As shown in FIG. 1, in at least one embodiment, the infusion pump battery capacity management and battery charge alert system includes an infusion pump 100 that internally includes and holds one or more rechargeable batteries and an infusion pump controller. In one or more embodiments, the infusion pump apparatus may include a speaker, a user interface 101 that may include a screen, for example a touch screen, one or more buttons and, may internally include and hold a computer, microprocessor, controller or any other type of programmable apparatus that may be coupled with the user interface 101.

In at least one embodiment, at least one detector 106 is configured to detect ambulation of the patient. The detector may include one or more of an input power sensor, an accelerometer and a wireless network interface. By way of one or more embodiments, the at least one detector 106 that detects the ambulation of the patient may include a sensor that detects removal of a power input from the infusion pump. In one or more embodiments, the accelerometer may be coupled with the computer such that the accelerometer detects acceleration indicative of ambulation of the patient coupled with the infusion pump. In at least one embodiment, the wireless network interface is coupled with the computer such that wireless interface detects wireless connectivity changes of the infusion pump 101 coupled with the patient.

According to one or more embodiments, during a programmed infusion, the at least one detector 106 may detect ambulation based on removal of a power input from the infusion pump 101 for less than 5 minutes, and one or more of sustained infusion pump movements for at least 10 seconds detected by the accelerometer, and infusion pump movement based on 3 events of wireless connectivity change detected by the wireless network interface. Other thresholds for these events in terms of the time duration or acceleration values or wireless connection changes are in keeping with the invention. For example, if the input power is lost as detected by the input power sensor, and the accelerometer detects accelerations over a predetermined threshold, or for example when integrated or double integrated show a velocity or movement over respective predetermined thresholds, or if wireless interface detects a number of wireless network changes over a predetermined threshold, then the patient ambulation may be indicated. In one or more embodiments, if any combinations of these values is detected or correlated, then ambulation may be indicated, and battery calculations may be undertaken in order to provide an alert related to battery capacity.

Figure 2:
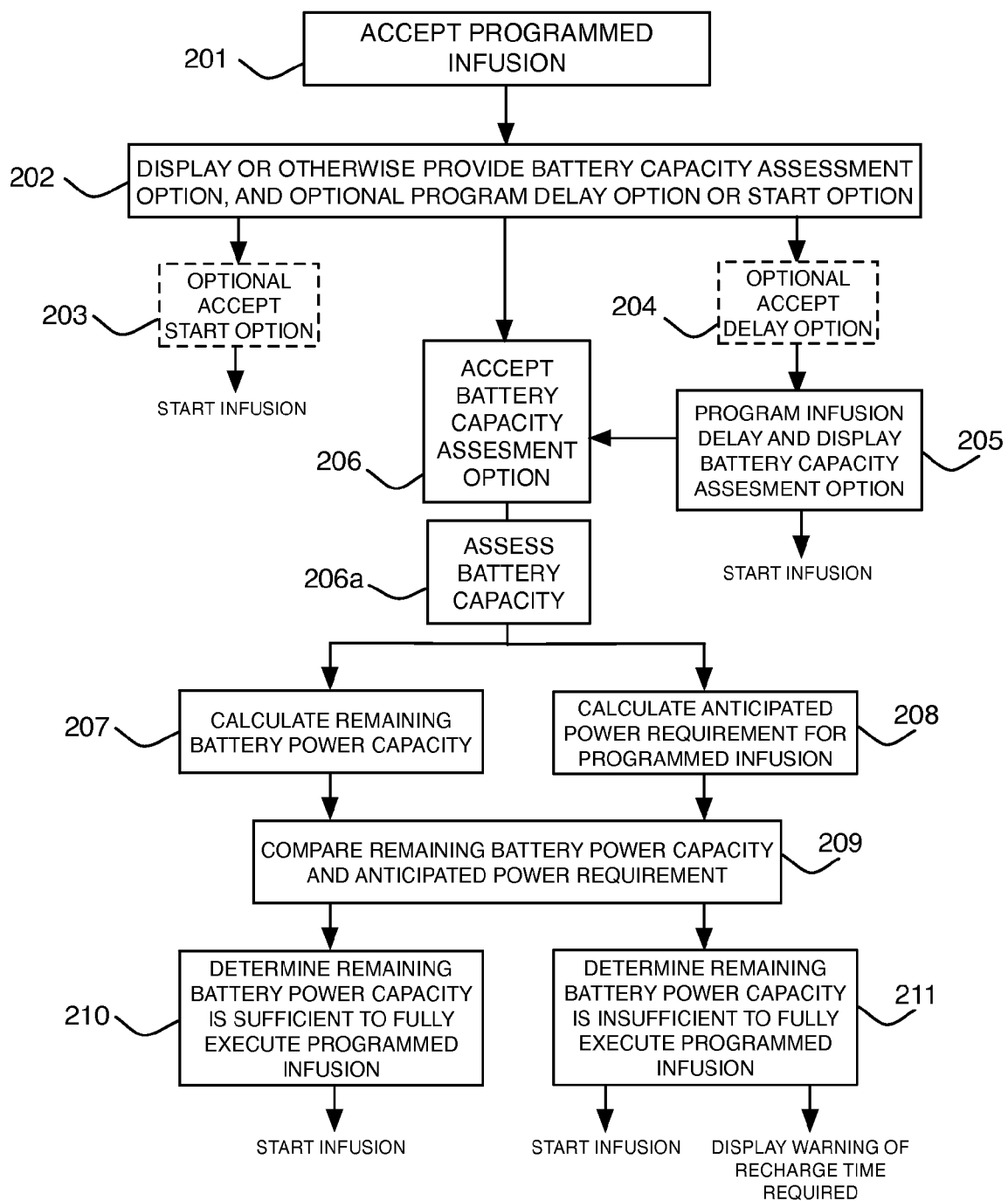
FIG. 2 illustrates a flow chart for the main elements of the system and method.

FIG. 2 illustrates a flow chart for the main elements of the system and method according to one or more embodiments of the invention. As shown in FIG. 2, by way of at least one embodiment of the invention, at step 201 the infusion pump 100 may accept an infusion input, wherein the infusion input includes a programmed infusion that may be input by one or more users via the infusion pump user interface 101. In another embodiment the programmed infusion can be electronically downloaded to the infusion pump 100 from a computer at location remote from the infusion pump. At step 201, in embodiments of the invention, the infusion pump controller may review the programmed infusion, and a result of the review may be presented on a confirmation screen of the user interface 101. At step 202, in one or more embodiments, the system may display or otherwise provide in any other manner a battery capacity assessment option, for example via user interface 101 that may display one or more of a start screen with a confirmation of the programmed infusion, a battery capacity assessment option, a program delay option, and a start option. In at least one embodiment, the infusion pump controller may accept a selection input to select one or more of the battery capacity assessment option, the program delay option and the start option, and assert a respective option.

In one or more embodiments, if the infusion pump controller asserts the start option 203, the programmed infusion may be executed via the infusion pump 100 and infusion is started. If the infusion pump controller asserts the delay option 204, in embodiments of the invention, an infusion delay may be programmed 205 and the infusion pump controller may then select the battery capacity assessment option or select the start option. If the infusion pump controller selects or asserts the battery capacity assessment option 206, in one or more embodiments, the infusion pump controller performs a battery capacity assessment at 206a and may calculate an anticipated power capacity requirement to execute the programmed infusion at 207, as a demand for example, calculate a remaining power capacity of the one or more rechargeable batteries at 208, as a supply for example, and compare the calculated anticipated power capacity requirement to the calculated remaining power capacity of the one or more rechargeable batteries at 209. According to at least one embodiment, the infusion pump controller may then determine whether the infusion pump is able to fully execute the programmed infusion based only on the remaining power capacity. In at least one embodiment of the invention, calculating an anticipated power capacity requirement to execute the programmed infusion may be based on a flow rate. Other inputs to a battery capacity assessment could include length of infusion, volume of infusion, pump backlight or wireless settings, user interface activity level, or any other parameter that effects power usage as one skilled in the art will recognize.

By way of one or more embodiments, if the infusion pump controller determines wherein the infusion pump may fully execute the programmed infusion using only the remaining power capacity at 210, the infusion pump controller may notify the one or more users, the infusion pump controller may assert the start option and the programmed infusion may be executed via the infusion pump only using the remaining power capacity, without the use of any charging or recharging. As such, in at least one embodiment, a user of the one or more users, such as a patient, may receive the prescribed and programmed infusion without further battery charging required, under the assumption wherein no significant changes to the programmed infusion and/or no significant changes to the user interface 101 are experienced. In at least one embodiment of the invention, the infusion pump controller may manage a plurality of infusions by available or remaining battery power capacity. According to at least one embodiment, if the infusion pump 101 is not in use, the infusion pump 101 may be charged such that at the start of a programmed or prescribed infusion, the one or more rechargeable batteries are at full charge.

If the infusion pump controller determines wherein the infusion pump may be unable to fully execute the programmed infusion only using the remaining power capacity at 211, in embodiments of the invention, the infusion pump controller may one or more of assert the start option, for example after accepting any type of input from a user, and the programmed infusion may be executed via the infusion pump 100, for example without the use of charging or recharging the one or more rechargeable batteries. In at least one embodiment, the infusion pump controller may accept any type of input that indicates that the user has opted to defer the recharging or charging, and/or may provide a warning to the one or more users wherein a recharge time, such as one or more partial recharge cycles or a full recharge cycle, may be required to fully execute the programmed infusion. In one or more embodiments, the warning may be a message that proactively alerts the user according to a recharge strategy without a typical audio "warning" or "alarm" for example.

In at least one embodiment of the invention, when the infusion pump controller determines wherein the infusion pump may be able to fully execute the programmed infusion only using the remaining power capacity at 210, the infusion pump controller may display the remaining power capacity that is sufficient to execute the programmed infusion on the user interface screen.

In one or more embodiments, the warning may be displayed as one or more notifications or messages on the user interface screen. The notification, in embodiments of the invention, may include wherein the remaining power capacity is insufficient to execute the programmed infusion, wherein a recharge time is required during execution of the programmed infusion, and a determination of a time before the one or more rechargeable batteries are depleted, or a determination of time before the one or more rechargeable batteries are depleted within a safety level, which may or not be user configurable. For example, the time before the one or more rechargeable batteries are depleted within a safety level may be about 30 minutes of remaining infusion or any other value within the scope of the invention. In one or more embodiments, the one or more rechargeable batteries may not provide sufficient power capacity to support the programmed infusion when the programmed infusion is, for example, of a longer duration than the one or more rechargeable batteries specifications, or because the one or more rechargeable batteries are not fully charged, or a combination of both. In at least one embodiment, the recharge time may include one or more of a partial-recharge of the one or more rechargeable batteries, or a full-recharge of the one or more rechargeable batteries.

Figure 3:
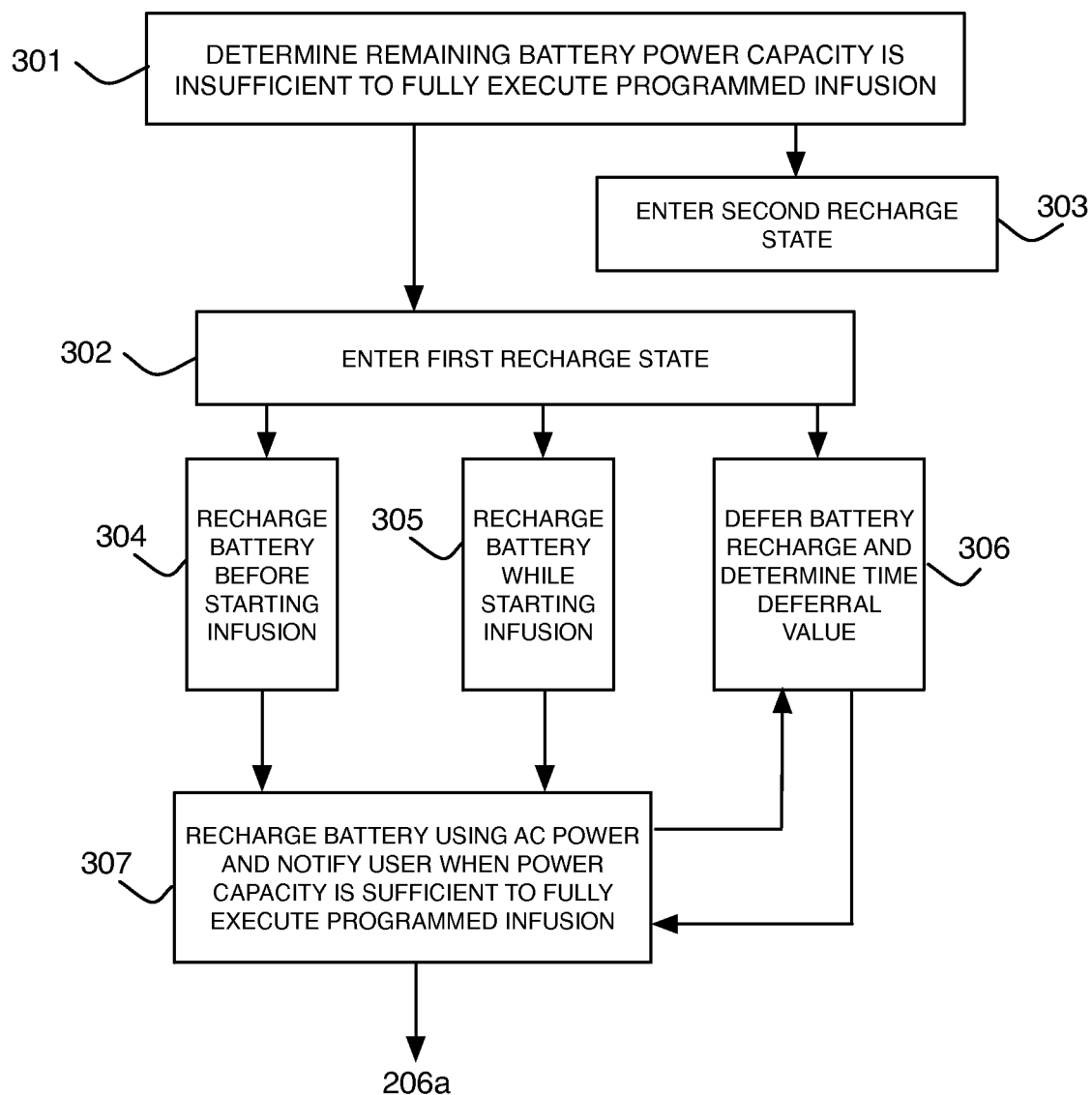
FIG. 3 illustrates a flow chart for the main elements of the system and method when an infusion pump programmer determines that the infusion pump is unable to fully execute a programmed infusion.

FIG. 3 illustrates a flow chart for the main elements of the system and method when an infusion pump programmer determines that the infusion pump is unable to fully execute a programmed infusion, according to one or more embodiments of the invention. As shown in FIG. 3, according to at least one embodiment, when the warning is provided wherein a recharge time is required to fully execute the programmed infusion after a determination is made wherein the remaining battery power capacity is insufficient to fully execute the programmed infusion at 301, the infusion pump may enter a first recharge state 302 or a second recharge state 303.

In one or more embodiments, the first recharge state at 302 may include a partial recharge of the one or more rechargeable batteries or a full recharge of the one or more rechargeable batteries, to fully execute the programmed infusion, and the second recharge state at 303 may include a full recharge of the one or more rechargeable batteries and a continuous recharge of the one or more rechargeable batteries during execution of the programmed infusion as a full recharge alone would not be sufficient to fully execute the programmed infusion. In at least one embodiment of the invention, the first recharge state may include wherein the remaining available battery power capacity may power the infusion pump 100 to execute the programmed infusion without a second recharge if the infusion pump is charged with a first recharge. In at least one embodiment of the invention, the second recharge state may include wherein the infusion pump may be incapable of executing the programmed infusion without a recharge period during the execution the programmed infusion, even if the one or more rechargeable batteries are fully charged prior to the start of the infusion and throughout.

In embodiments of the invention, the first recharge state and the second recharge state may include plugging the infusion pump into the an AC power source to partially recharge the one or more rechargeable batteries, fully recharge the one or more rechargeable batteries or continuously recharge the one or more rechargeable batteries. In one or more embodiments, during the first recharge state and the second recharge state, the infusion pump controller, via the one or more users, may apply a partial recharge, before or during the executed programmed infusion, that may be sufficient to power the infusion fully, and minimize the time the one or more users, such as a patient, may need to connect to AC power, compared to a full recharge. As such, the quality of life is improved as the patient's time tethered to AC power is minimized.

According to at least one embodiment, the one or more rechargeable batteries may not need to be fully charged in order to fully execute the programmed infusion, wherein a well-timed partial recharge during infusion may be short and effective. For example, while the infusion pump 100 may be fully charged in about 4 hours, the infusion pump 100 reaches 85% of charge within about 2.5 hours and as such, charge of about 30 minutes to 60 minutes strategically aligned and implemented in the infusion may be sufficient to increment the available remaining battery power capacity to fully execute the programmed infusion, safely and accurately.

In at least one embodiment, during the first recharge state, the infusion pump controller may partially or fully recharge the one or more rechargeable batteries before execution of the programmed infusion at 304, or partially or fully recharge the one or more rechargeable batteries during execution of the programmed infusion at 305. After a recharge cycle before execution of the programmed infusion 304 or after the recharge cycle begins while starting infusion at 305, the infusion pump controller may recharge the one or more rechargeable batteries using AC power and the infusion pump controller may notify the one or more users when the remaining power capacity of the one or more batteries is sufficient to fully execute the programmed infusion at 307. In at least one embodiment, the infusion pump controller may then execute and start the infusion or continue the infusion at 308. For example, the infusion pump 100 may be charged using AC power until the remaining and current battery power capacity is sufficient to fully execute the programmed infusion, with a margin of safety as needed without the need for a full recharge to maximum available remaining battery power capacity. As such, the infusion pump controller may notify the one or more users when the AC power may be disconnected since sufficient battery power capacity is available to complete the programmed infusion. In at least one embodiment, a user of the one or more users may opt to exit prior to sufficient recharge of the one or more rechargeable batteries. In one or more embodiments, the battery capacity is at least periodically assessed at 206a for example based on any or all parameters that may affect power usage for example as previously stated.

In one or more embodiments, during the first recharge state, the infusion pump may defer the partial or full recharge of the one or more rechargeable batteries via the one or more users at 306, wherein the infusion pump may determine a time deferral value and notify the one or more users with the determined time deferral value and wherein the determined time deferral value may be a value that allows the infusion pump to remain to operate safely before requiring the partial recharge or the full recharge. The deferred recharge, in one or more embodiments, by the one or more users, may occur during execution of the programmed infusion. In at least one embodiment, during the deferral stage 306, the infusion pump controller may notify the one or more users wherein remaining available battery power capacity is insufficient to fully execute the programmed infusion. The notification may also suggest a time to recharge and duration of recharge at that time to ensure that the infusion may complete, which is unknown in the art.

After the deferral stage 306, the infusion pump controller may recharge the one or more rechargeable batteries using AC power and the infusion pump controller may notify the one or more users when the remaining power capacity of the one or more batteries is sufficient to fully execute the programmed infusion and that the AC power may be disconnected, with or without a full recharge of the one or more rechargeable batteries. In at least one embodiment, a user of the one or more users may opt to exit prior to sufficient recharge of the one or more rechargeable batteries, and defer the recharge and start infusion at step 308. In embodiments of the invention, during an AC power recharge time, or after an AC power recharge time has elapsed, at 307, the infusion pump controller may continue to defer the partial or full recharge of the one or more rechargeable batteries via the one or more users at 306 and may start the infusion or continue the infusion at 308.

During step 306, in one or more embodiments, a user of the one or more users, such as a patient, may notify the infusion pump 100 of a preferred recharge start time and the patient may receive output from the infusion pump controller on the likely charge time required to increment the necessary remaining battery power capacity. In at least one embodiment, the patient may enter a continuous charge time value available (for example, 45 minutes), wherein the infusion pump controller may receive such an input and output a recommendation of an optimal start time for the recharge period and/or an acceptable recharge start time range. By way of one or more embodiments, the user interface screen may indicate that a partial recharge is required to fully execute or complete the programmed infusion or that sufficient battery power capacity remains to fully execute the programmed infusion. In at least one embodiment, the infusion pump 100 may include a power capacity management software to calculate the anticipated power capacity requirement to execute the programmed infusion, to calculate the remaining power capacity of the one or more rechargeable batteries and to compare the calculated anticipated power capacity requirement to the calculated remaining power capacity of the one or more rechargeable batteries. According to at least one embodiment, the power capacity management software may be used for determining whether the infusion pump is able to fully execute the programmed infusion based only on the remaining power capacity, as discussed above. This enables the user to minimize the amount of time that the batteries are coupled to an external power source, which is unknown in the art. This gives the user the freedom to remain mobile for the maximum amount of time as well. In one or more embodiments, the power capacity management software may be actively available or disabled.

Figure 4:
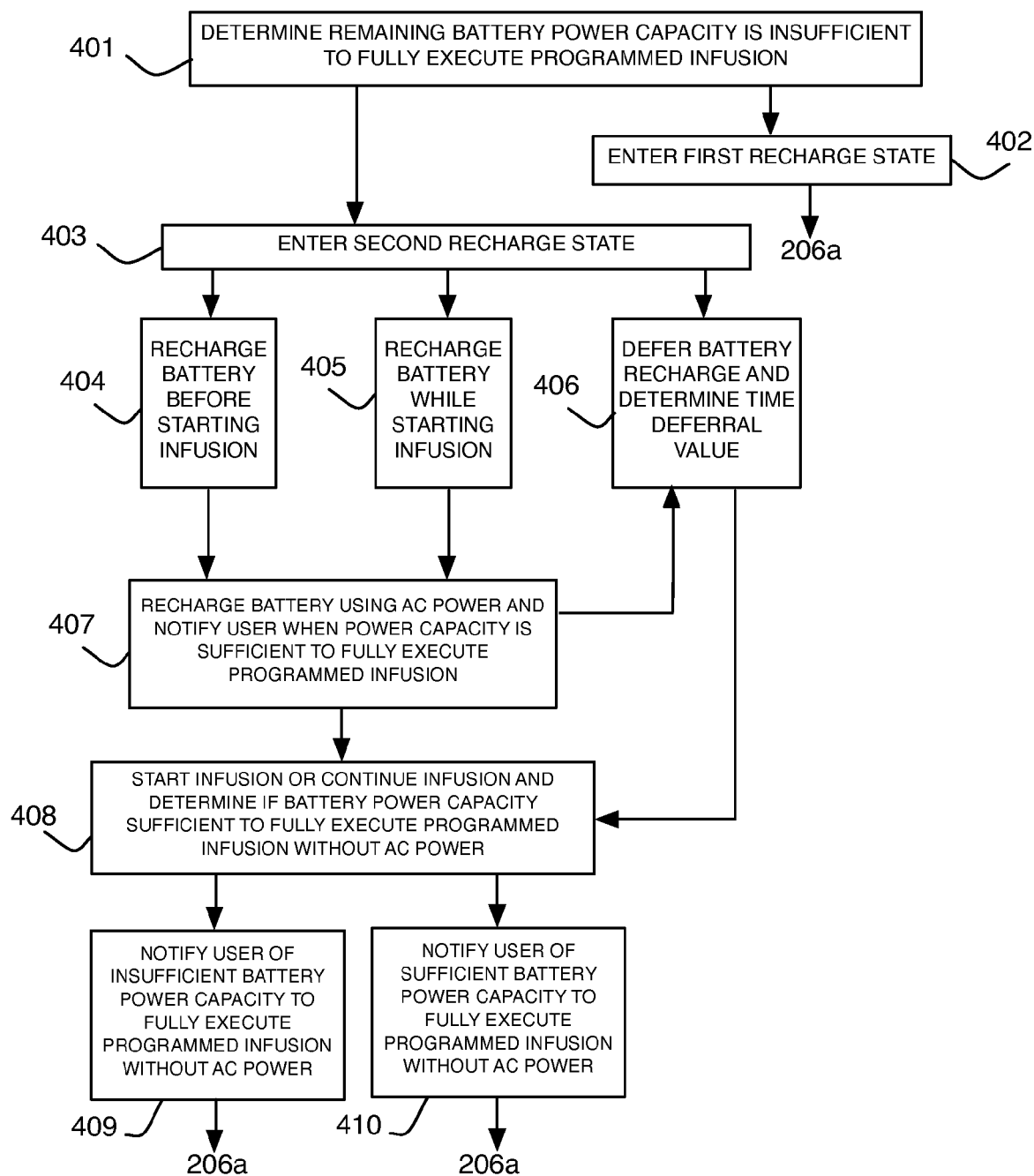
FIG. 4 illustrates a flow diagram for the main functional elements of the system and method when an infusion pump programmer determines that the infusion pump is unable to fully execute a programmed infusion and a recharge period is required.

FIG. 4 illustrates a flow diagram for the main functional elements of the system and method when an infusion pump programmer determines that the infusion pump is unable to fully execute a programmed infusion and a recharge period is required, according to one or more embodiments of the invention. As shown in FIG. 4, and stated above regarding FIG. 3, when the warning is provided wherein a recharge time is required to fully execute the programmed infusion after a determination is made wherein the remaining battery power capacity is insufficient to fully execute the programmed infusion at 401, the infusion pump may enter a first recharge state 402 or a second recharge state 403, as discussed above regarding FIG. 3. According to at least one embodiment, during the second recharge state, the infusion pump controller may recharge the one or more rechargeable batteries by partially or fully recharging the one or more rechargeable batteries before execution of the programmed infusion and then continuously charging the one or more rechargeable batteries during execution of the programmed infusion at 404, or partially or fully recharging the one or more rechargeable batteries during execution the programmed infusion and continuously charging the one or more rechargeable batteries during execution of the programmed infusion 405. In at least one embodiment, the infusion pump controller may defer the recharge of the one or more rechargeable batteries and start or continue infusion at 408. In one or more embodiments, during the deferral recharge stage 406, the infusion pump may determine a time deferral value and may notify the one or more users with the determined time deferral value, for example by utilizing the same logic in block 407, wherein the determined time deferral value may be a value that allows the infusion pump to remain to operate safely before requiring the partial recharge or the fully recharge. Depending on the length of the infusion and battery capacity and requirements, the user may be notified to connect with a power source multiple times during the infusion.

During step 407, in one or more embodiments, a user of the one or more users, such as a patient, may notify the infusion pump 100 of a preferred recharge start time and the patient may receive input from the infusion pump controller on the likely charge time required to increment the necessary remaining battery power capacity. This enables the user to pre-plan their recharge when for example they know they may be stationary, such as during a meal or when observing a television broadcast that occurs at a known time. In at least one embodiment, the patient may enter a continuous charge time value available, wherein the infusion pump controller may receive such an input and output a recommendation of an optimal start time for the recharge period and/or an acceptable recharge start time range. By way of one or more embodiments, the user interface screen may indicate wherein a partial recharge is required to fully execute or complete the programmed infusion or that sufficient battery power capacity remains to fully execute the programmed infusion. In at least one embodiment, the infusion pump 100 may include a power capacity management software to calculate the anticipated power capacity requirement to execute the programmed infusion, to calculate the remaining power capacity of the one or more rechargeable batteries and to compare the calculated anticipated power capacity requirement to the calculated remaining power capacity of the one or more rechargeable batteries. According to at least one embodiment, the power capacity management software may be used for determining whether the infusion pump is able to fully execute the programmed infusion based only on the remaining power capacity, as discussed above. In one or more embodiments, the power capacity management software may be actively available or disabled.

Embodiments of the invention may include plugging the infusion pump into an AC power source or other external power source to partially recharge the one or more rechargeable batteries, fully recharge the one or more rechargeable batteries or continuously recharge the one or more rechargeable batteries. At 407, after a recharge before execution of the programmed infusion 404, or after the recharge begins while starting infusion at 405, the infusion pump controller may recharge the one or more rechargeable batteries using AC power and the infusion pump controller may notify the one or more users when the remaining power capacity of the one or more batteries is sufficient to fully execute the programmed infusion. In one or more embodiments, the infusion pump controller may notify the one or more users via the user interface screen, using one or more on-screen icons, wherein the one or more rechargeable batteries are fully charged, and may notify the one or more users via the user interface screen, using another icon of the one or more on-screen icons, wherein insufficient battery power capacity is available to fully execute the programmed infusion. As such, the infusion pump controller notified the one or more users wherein a full recharge of the one or more rechargeable batteries is insufficient to fully execute the programmed infusion, and multiple recharges are required.

In at least one embodiment, the infusion pump controller may then execute and start the infusion or continue the infusion, and may determine if battery power capacity is not sufficient to fully execute the programmed infusion without coupling the batteries to an external power source such as AC power, at 408. If the infusion pump controller determines wherein there is insufficient battery power capacity to fully execute the programmed infusion with AC power, the infusion pump controller may notify the one or more users at 409. If the infusion pump controller determines wherein there is sufficient battery power capacity to fully execute the programmed infusion with AC power, the infusion pump controller may notify the one or more users at 410. In either case, the battery capacity may be at least periodically assessed at 206a.

By way of one or more embodiments, the infusion pump controller may periodically calculate the remaining battery power capacity, or when any specific infusion parameters or any other system parameters described elsewhere herein are made for example and calculate the anticipated power capacity required to fully execute the infusion, and full battery power capacity. According to at least one embodiment, after the one or more users are notified wherein there is sufficient battery power capacity to fully execute the programmed infusion with AC power, the infusion pump controller may enter the first recharge state 402, wherein the infusion pump controller may begin the process as illustrated in FIG. 3 and discussed above regarding entering the first recharge state at 302. At any time, during the first or second recharge state, the battery capacity may be assessed at 206a. As such, a single appropriate recharge is sufficient to fully execute the programmed infusion. In one or more embodiments, if the infusion pump controller determines wherein the one or more rechargeable batteries have low battery power capacity remaining, the infusion pump controller may notify the one or more users that a recharge is required. As such, when entering the first recharge state at 402, or 302 of FIG. 3, the infusion pump 100 may be plugged into an AC power outlet and the infusion pump controller may notify the one or more users wherein AC power is needed.

One or more embodiments of the invention may include the ability to select or enable/disable select features to align or otherwise make the infusion pump consistent with the clinical practices of a facility, or a care area within a facility. For example, features such as occlusion pressure alarm threshold, air-in-line alarm threshold, hard dose or flow rate limits, key volume, alarm volume, backlight settings, pump unattended message timing, infusion near end message timing and KVO (keep vein open) rate, may be configured on the pump. Typically configuration is thru selection from a range of allowable settings. Similarly, features such as delayed start, loading dose, and post occlusion auto-restart may be enabled or disabled. Configurations typically define the default settings for a pump, replacing factory default settings and aligning the features of the pump with clinical practices or preferences of the facility, care area, or clinician. These configurations may be modified by the clinician at the point of use, or may require a reconfiguration by an authorized technician to be changed. Embodiments may provide the option to alter the configuration, require or make the configuration unavailable or any combination thereof over time. The configuration setting feature may also be initially enabled or disabled at the factory default level. As these settings may influence power usage, embodiments of the invention may utilize the settings and detect changes thereto and recalculate estimated battery usage in order to determine whether the remaining battery power capacity is insufficient to fully execute a programmed infusion at 301 or 401 for example. In other embodiments, the battery capacity checking and warning behavior of the present invention can itself be configurable with user customizable settings on the pump or in a drug library formulated for download to the infusion pump. A user selectable setting in a drug library editor on a remote computer can switch the battery capacity checking and warning behavior off or on for an individual infusion program, for a given pump or pump type, for a given clinical care area of a facility, or for a given patient or therapy type. In other embodiments, various parameters of the battery capacity checking and warning behavior of the present invention also can be configured in the drug library, including but not limited to frequency of calculation and/or comparison, addressing and text of warning messages, trigger points or values for sufficient and insufficient capacity, and duration and number of charges or recharges permitted or suggested. These drug library settings related to battery capacity checking, warning and charging behavior can be configured to be modifiable at the infusion pump by the user or not.

According to one or more embodiments of the invention, the infusion pump 100, utilizing one or more rechargeable batteries, may be utilized for longer periods of infusion time (for example greater than 24 or 48 hours) and for infusions requiring high fluid volume capacity. In addition, in embodiments of the invention, the infusion pump 100 may reduce any environment burdens of routine use of disposable batteries, and may enable the patient to optimize time required tethered to the AC power outlet to ensure one or more infusion pump therapies are safely provided while minimizing any practical burden on the one or more users, such as the patient.

Figure 5:
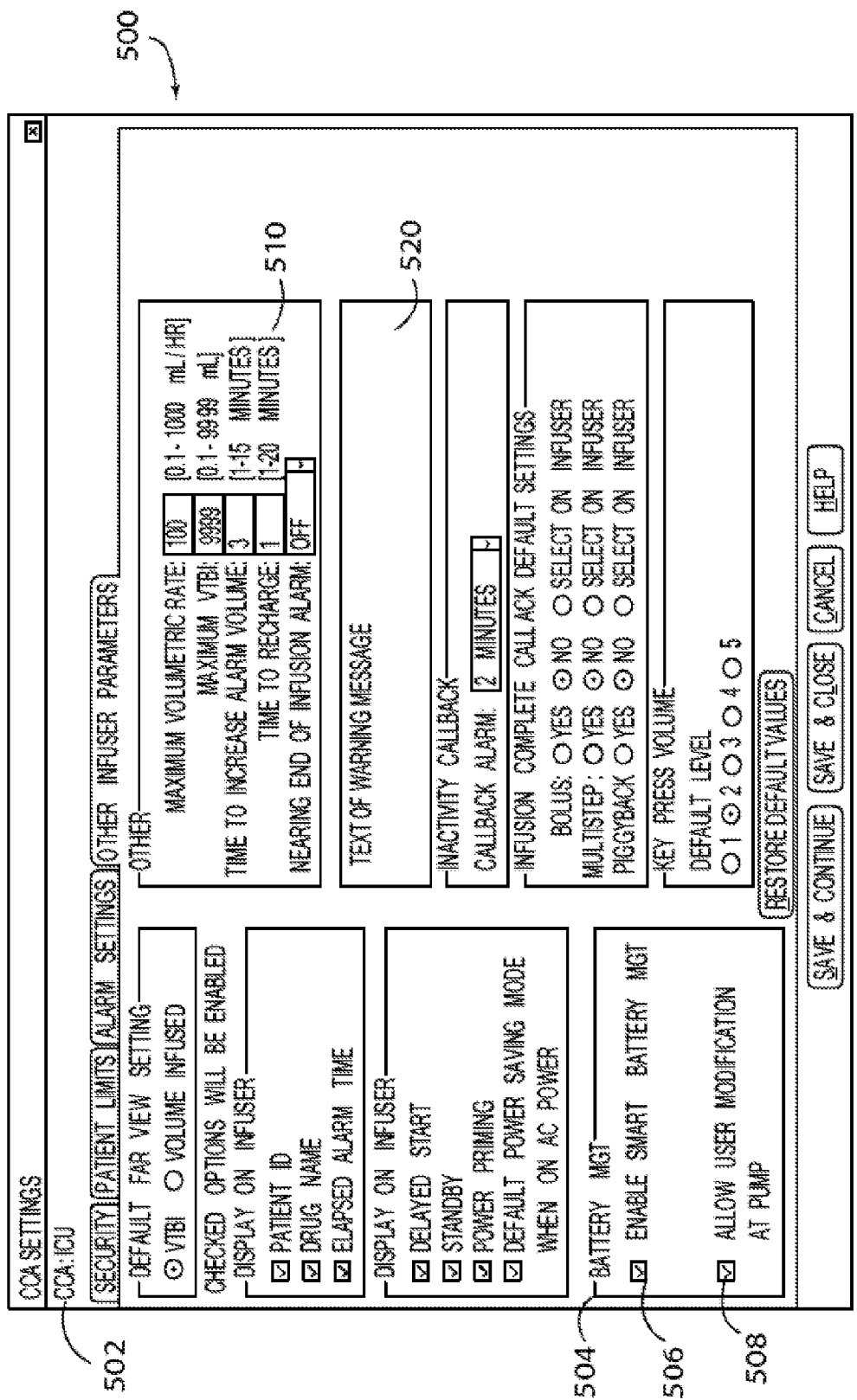
FIG. 5 illustrates an embodiment of the infusion parameters screen in a drug library editor.

FIG. 5 illustrates an embodiment of the infusion parameters screen 500 for example as configured via a drug library editor hosted on a remote computer. As shown, infusion parameters may be set for a clinical care area, such as an intensive care unit at 502. The parameters may include battery management parameters 504 that may further include user interface elements to enable smart battery management at 506 and as described in detail above, as well as allow the user to modify battery parameters at the pump at 508. The parameters may also include including the user interface elements related to the time to recharge 510 and the text of warning message 520 and any other parameters based on the particular implementation as one skilled in the art will recognize.

Figure 6:
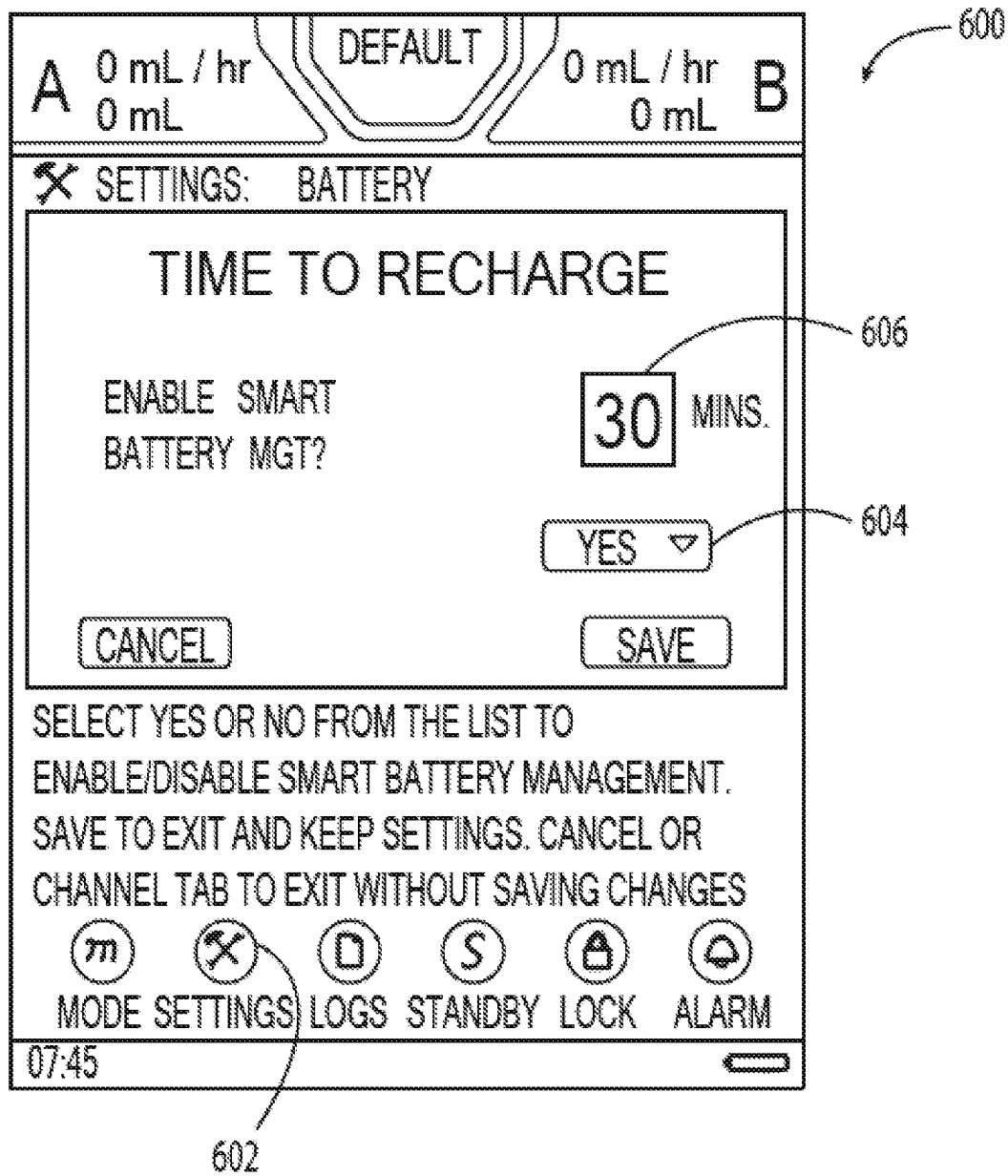
FIG. 6 illustrates an embodiment of the battery settings screen on a pump.

FIG. 6 illustrates an embodiment of the battery settings screen 600 on the pump, for example for setting battery management parameters as enabled in one or more embodiments as per 508 in FIG. 5. For example, the battery settings 602 may include the enable smart battery management setting at 604 and time to recharge at 606 similar to the remote settings described in relation to the drug library editor shown in FIG. 5.

Figure 7:
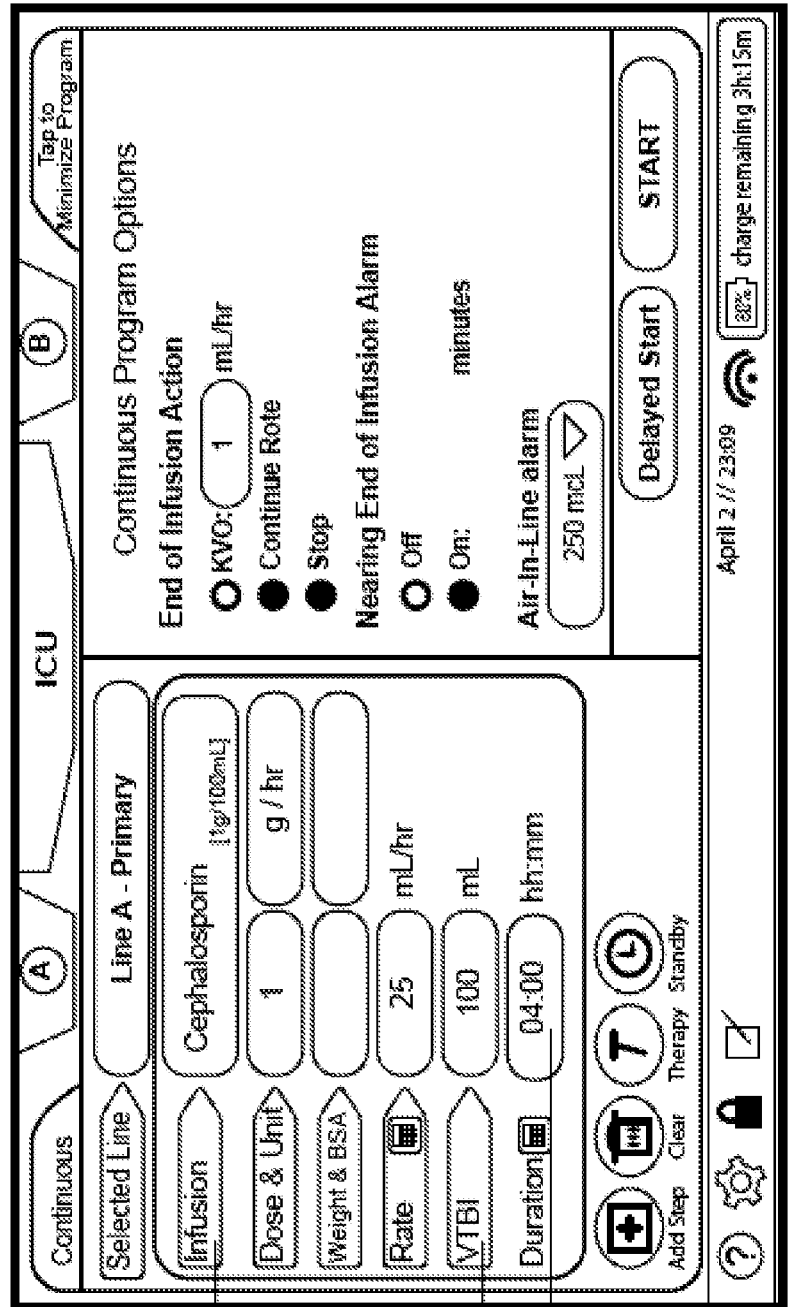
FIG. 7 shows an illustrative diagram of an infusion pump user interface screen.

FIG. 7 shows an illustrative diagram of an infusion pump user interface screen, according to one or more embodiments of the invention. As shown in FIG. 7, by way of at least one embodiment, the infusion pump 101 may accept an infusion input that includes a programmed infusion by one or more users via the infusion pump user interface 103 shown in FIG. 1. In one or more embodiment, the infusion pump user interface 103 may include inputs such as soft buttons, or be implemented as a touch screen or any other type of input interface and for example use the display on the user interface screen 104. In one or more embodiments, the infusion pump user interface screen 104 may include one or more of a start screen with a confirmation of the programmed infusion, a start option, a program delay option, a battery charge indicator 160 and requirements of the programmed infusion 140. In at least one embodiment of the invention, the battery charge indicator 160 may indicate remaining power capacity of the one or more rechargeable batteries 102 as at least one of a percentage, a time including hours and minutes, or both the percentage and time. Other time units such as days and seconds or any other temporal unit may be indicated or displayed.

In one or more embodiments, when the infusion pump 101 is plugged into a power input, such as an AC power source, the user interface screen 104 indicates via the battery charge indicator 160 wherein the infusion pump 101 is being charged. In at least one embodiment, once the infusion pump 101 is disconnected from the power input, such as a main power source, the battery status symbol of the battery charge indicator 160 updates to display the amount of charge remaining, in one or more of hours and minutes and percentage, as well as the estimated time remaining for battery operation for the programmed infusion. In one or more embodiments, when the at least one detector 106 detects ambulation, the user interface 103 may highlight a "charge remaining" message at the user interface screen 104, and may be further accentuated by an audible message, such as via a beep or melody tone.

According to one or more embodiments of the invention, when the at least one detector 106 detects patient ambulation, the infusion pump controller 105 may calculate a required remaining duration 150 of the programmed infusion to fully execute the programmed infusion, and display the calculated required remaining duration 150 of the programmed infusion on the user interface screen 104. In at least one embodiment, the infusion pump controller 105 may calculate an anticipated power capacity requirement to fully execute the programmed infusion, and may calculate a remaining power capacity of the one or more rechargeable batteries. In one or more embodiments, the infusion pump controller 105 may compare the calculated anticipated power capacity requirement to the calculated remaining power capacity of the one or more rechargeable batteries, and therefrom determines whether the infusion pump 101 is able to fully execute the programmed infusion based on a comparison of the calculated required remaining duration 150 of the programmed infusion and the calculated remaining power capacity of the one or more rechargeable batteries 102.

In one or more embodiments, the requirements of the programmed infusion 140 may include one or more of a type of drug in the fluid, a dosage, a flow rate and volume to be infused. In at least one embodiment, the pump controller 105 may calculate an anticipated power capacity requirement to execute the programmed infusion based on one or more of the type of drug, the dosage, the flow rate and the volume to be infused.

In at least one embodiment of the invention, one or more of the calculated required remaining duration 150 of the programmed infusion, the anticipated power capacity requirement to fully execute the programmed infusion, the remaining power capacity of the one or more rechargeable batteries and the determination of whether infusion pump 101 is able to fully execute the programmed infusion based on a comparison of the calculated required remaining duration 150 of the programmed infusion and the calculated remaining power capacity of the one or more rechargeable batteries 102, may occur prior to the start of the programmed infusion or during the progress of the programmed infusion.

In one or more embodiments, the calculated anticipated power capacity requirement to fully execute the programmed infusion and the calculated remaining power capacity of the one or more rechargeable batteries 102, that may be calculated in mAh, may include one or more parameters such as infusion pump motor speed and screen backlight. In at least one embodiment, the calculated remaining power capacity of the one or more rechargeable batteries may include a margin of error for the benefit of the one or more users and patient safety, for example wherein the battery 102 may be able to last a duration of 4 hours, as calculated, however the display estimate on the user interface screen 102 is decreased to 3 hours and 15 minutes.

By way of at least one embodiment, the displayed calculated remaining power capacity of the one or more rechargeable batteries 102 may be visually accentuated, such as highlighted, and/or may be accompanied by an audible or vibratory alert, to draw the one or more user's attention.

Figure 8:
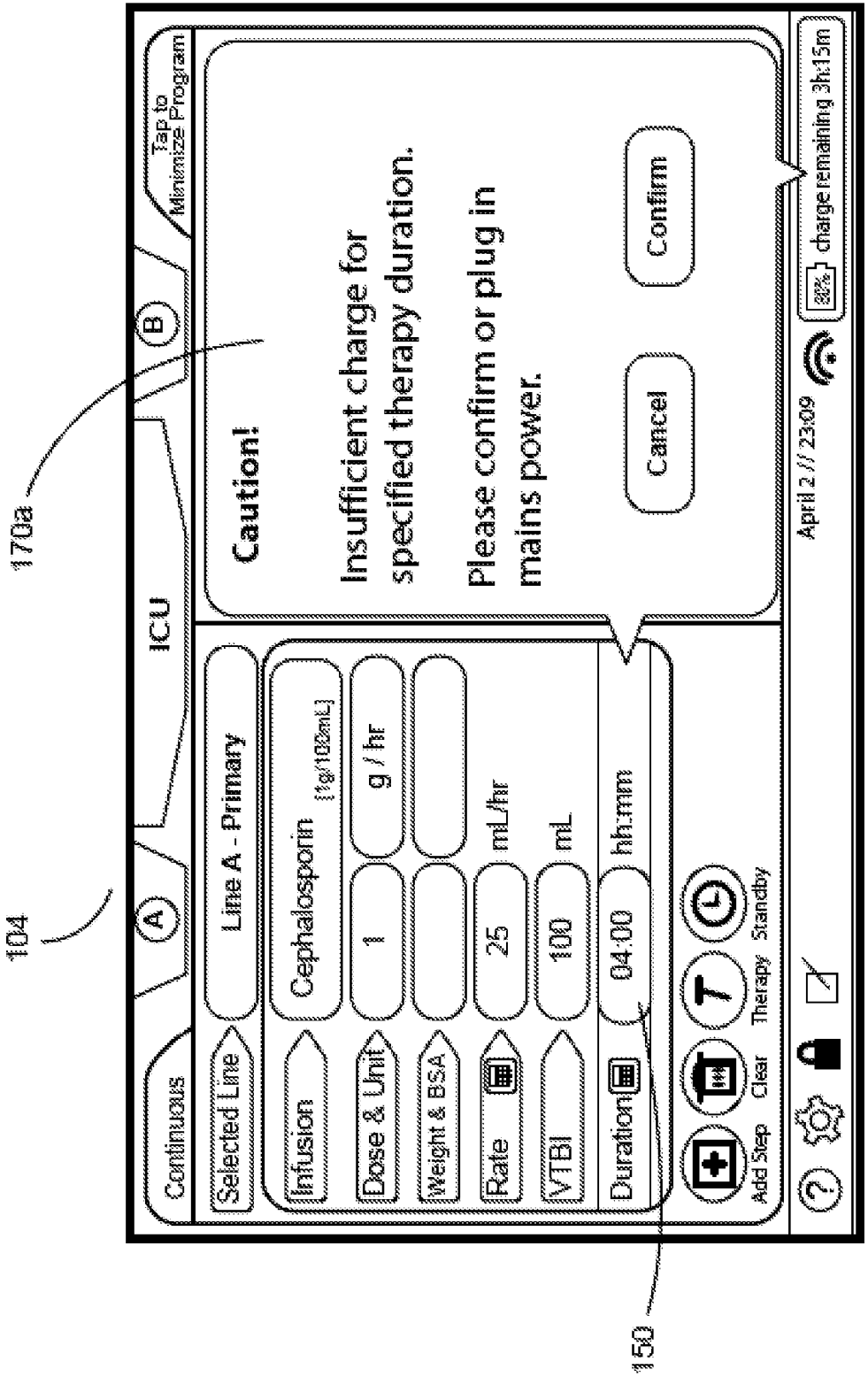
FIG. 8 shows an illustrative diagram of the infusion pump user interface screen displaying a warning.

FIG. 8 shows an illustrative diagram of the infusion pump user interface screen 104 displaying a warning, according to one or more embodiments of the invention. According to at least one embodiment, if the infusion pump controller 105 determines wherein the infusion pump 101 is able to fully execute the programmed infusion with the required remaining duration 150 of the programmed infusion using only the remaining power capacity, then the infusion pump controller 105 asserts the start option as shown in FIG. 2 and the programmed infusion is executed via the infusion pump 101.

However, as shown in FIG. 8, according to one or more embodiments, if the infusion pump controller 105 determines wherein the infusion pump 101 is unable to fully execute the programmed infusion with the required remaining duration 150 of the programmed infusion only using the remaining power capacity, then the infusion pump controller 105 provides a warning 170a to the one or more users, on the user interface screen 104, indicating insufficient remaining power capacity.

In at least one embodiment, the warning 170a may require input from the one or more users to confirm a desired action, acknowledging or confirming that the battery may run out of power before the programmed infusion or therapy is finished. In one or more embodiments, such an acknowledgement or confirmation may be accepted or unaccepted via a "confirm" or "cancel" option button provided on the user interface screen 104.

In at least one embodiment of the invention, when the infusion pump controller 105 determines wherein the infusion pump 101 is unable to fully execute the programmed infusion with the required remaining duration of the programmed infusion only using the remaining power capacity, the infusion pump controller 105 may provide one or more of a duration of charge required of the one or more rechargeable batteries 102 prior to starting the programmed infusion to fully execute the programmed infusion with the required remaining duration 150 of the programmed infusion, and an anticipated time when a recharge of the one or more rechargeable batteries 102 of the infusion pump 101 is required during execution of the programmed infusion to fully execute the programmed infusion with the required remaining duration 150 of the programmed infusion.

Figure 9:
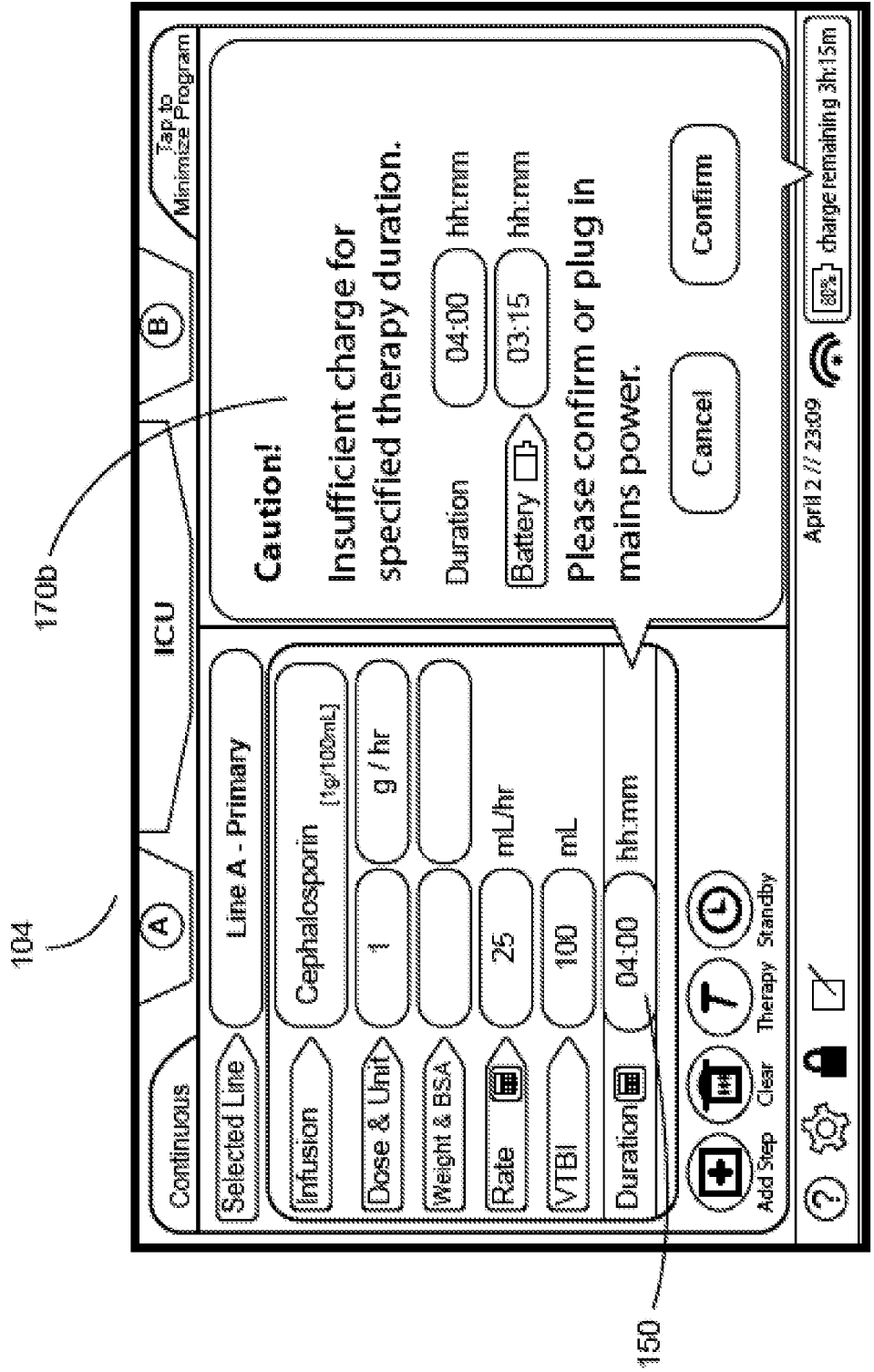
FIG. 9 shows an illustrative diagram of the infusion pump user interface screen displaying a remaining duration of a programmed infusion and remaining power capacity of one or more rechargeable batteries.

FIG. 9 shows an illustrative diagram of the infusion pump user interface screen 104 displaying a remaining duration of a programmed infusion and remaining power capacity of one or more rechargeable batteries, according to one or more embodiments of the invention. By way of at least one embodiment, when the infusion pump controller 105 determines wherein the infusion pump 101 is unable to fully execute the programmed infusion with the required remaining duration 150 of the programmed infusion only using the remaining power capacity, the infusion pump controller 105 may provide a second warning 170b to the one or more users, on the user interface screen 104, indicating wherein the infusion pump 101 is required to be plugged in or re-connected to a main power source, such as an AC power source.

In at least one embodiment, prior to the start of the programmed infusion and after the one or more users select the "start" option for the programmed infusion, the warning 170b may require input from the one or more users to confirm a desired action, acknowledging or confirming that the battery may run out of power before the programmed infusion or therapy is finished. In one or more embodiments, such an acknowledgement or confirmation may be accepted or unaccepted via a "confirm" or "cancel" option button provided on the user interface screen 104. In one or more embodiments, the warning 170b may occur during the progress of the programmed infusion when the infusion pump 101 is unplugged or is required to be plugged in or re-connected to a main power source, such as an AC power source. If the cancel button is selected, the therapy program would be cancelled or the user may be taken to the program or titration screen to make adjustments to the therapy if desired.

In at least one embodiments, the warnings, such as warning 170a and warning 170b, may be cautionary messages that include one or both of the remaining programmed infusion duration 150 and the remaining battery life or battery power capacity, relative to the programmed infusion.

In one or more embodiments, the infusion pump controller 105 may differentiate between a main power input disconnection and ambulation, such that different alerts or warnings may be utilized to inform the one or more users of the disconnection or the ambulation. In at least one embodiment, prioritization of the different cautions, or warnings, or alerts may be used to more effectively differentiate between events that are impacted by or related to the charge of the one or more batteries 102. For example, in one or more embodiments:

TABLE 1

| Conditions | Priority | Alert Type |
|---|---|---|
| Ambulation Detected Program Time Remaining > Charge Remaining | Highest | Caution statement on user interface screen requiring the user to confirm |
| Disconnection From Main Power Program Time Remaining > Charge Remaining | High | Caution statement on user interface screen disappearing after 5 seconds. User confirmation is not required |
| Ambulation Detected Program Time Remaining < Charge Remaining | Medium | Charge remaining is displayed on user interface screen, highlighted and accompanied by an audible message |
| Disconnection From Main Power Program Time Remaining < Charge Remaining | Low | Charge remaining is displayed on user interface screen |

As the infuser is unplugged from mains power, without ambulation detected, the infuser alerts the user with an onscreen message if the remaining duration of therapy exceeds the estimated charge remaining for the battery.

Figure 10:
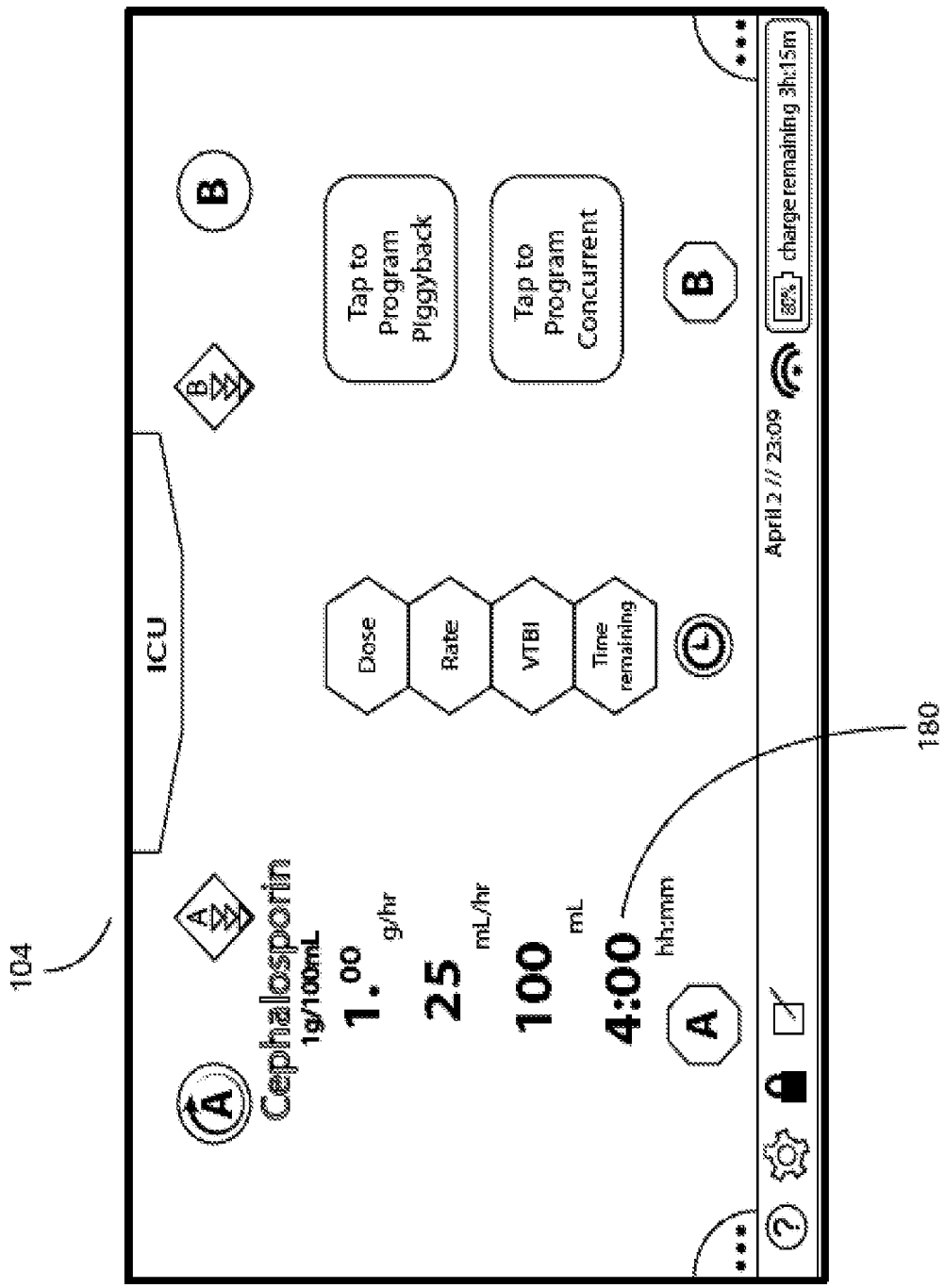
FIG. 10 shows an illustrative diagram of the infusion pump user interface screen displaying a time-remaining counter for the programmed infusion and remaining power capacity of one or more rechargeable batteries.
Figure 11:
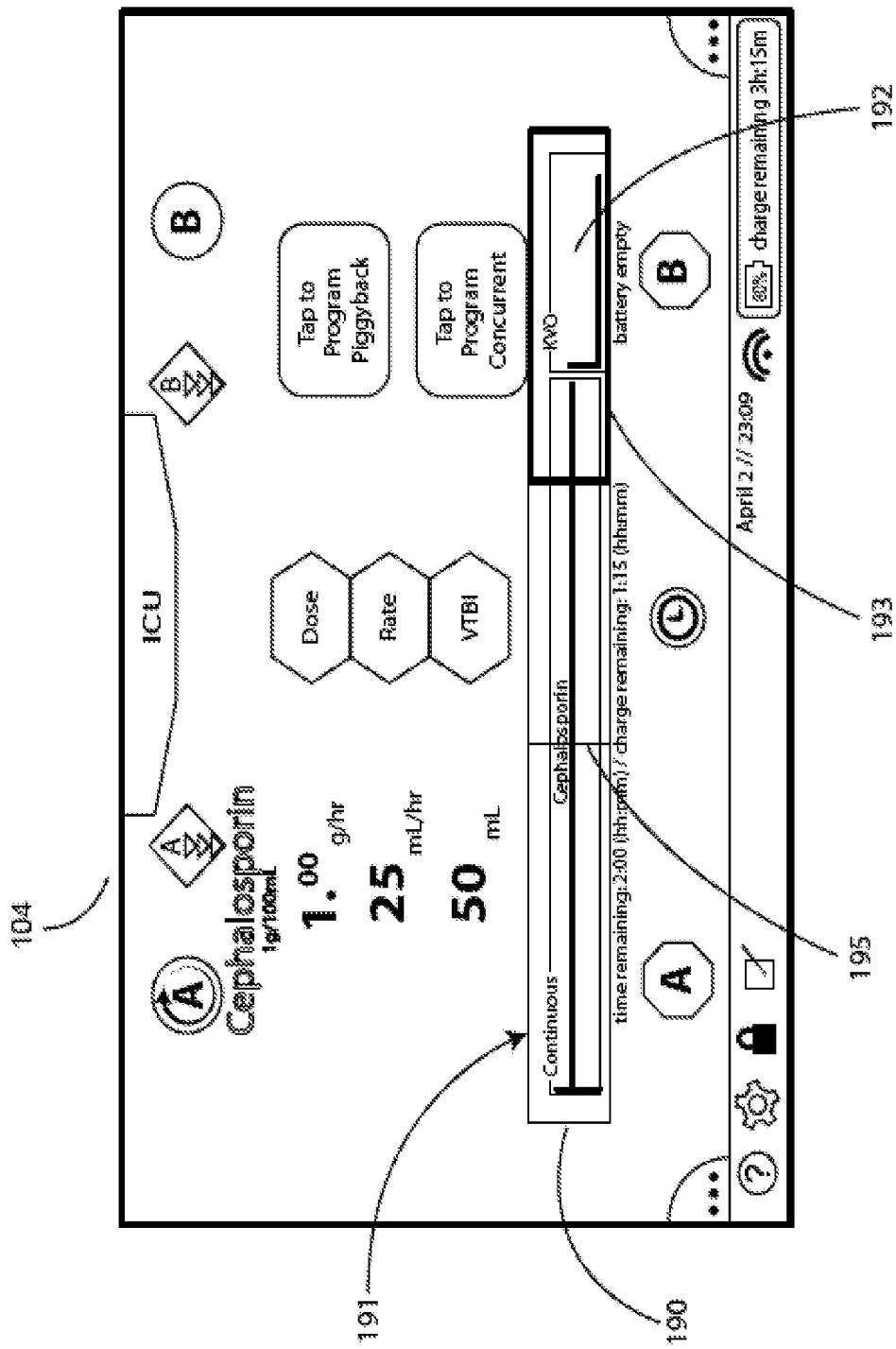
FIG. 11 shows an illustrative diagram of the infusion pump user interface screen displaying a therapy-progress bar for the programmed infusion and remaining power capacity of one or more rechargeable batteries.

FIG. 10 shows an illustrative diagram of the infusion pump user interface screen 104 displaying a time-remaining counter 180 for the programmed infusion and FIG. 11 shows an illustrative diagram of the infusion pump user interface screen displaying a therapy-progress bar 190 for the programmed infusion, according to one or more embodiments of the invention.

In at least one embodiment, the one or more users may choose to start the programmed therapy, whether sufficient battery charge is available to sustain the infusion for the entire duration, or not. In addition to or as an alternative to the remaining duration of the programmed infusion 150, the one or more infusion requirements 140 such as dose, rate, weight, and VTBI parameters, may be used to estimate whether the programmed infusion or therapy may be completely powered by the estimated or calculated charge or battery power capacity remaining to fully execute the programmed infusion.

As shown in FIG. 10 and FIG. 11, according to at least one embodiment, the infusion pump 101 may display on the user interface screen 104 one or more of a time-remaining counter 180, in the hours and minutes, that displays the calculated required remaining duration 150 of the programmed infusion to fully execute the programmed infusion, and/or may include a therapy-progress bar 190. In at least one embodiment, as shown in FIG. 11, the therapy-progress bar 190 may include one or more of the calculated required remaining duration 150 of the programmed infusion to fully execute the programmed infusion, the calculated remaining power capacity of the one or more rechargeable batteries 102, and a bar graph displaying a moving bar indicating the progress of the programmed infusion.

In one or more embodiments of the invention, the bar graph 190 may include one or more of a first segment 191 displaying a continuous infusion time of an infusion, a second segment 192 displaying a keep vein open (KVO) time, and a third segment 193 highlighted along one or more of the first segment 191 and the second segment 192 that indicates when the remaining power capacity of the one or more rechargeable batteries 102 will be essentially exhausted. In one or more embodiments, the third segment 193 may be highlighted using a different color or pattern to clearly distinguish the third segment 193 from the first segment 191 and the second segment 192. As such, in one or more embodiments, the user may easily observe that the state when the one or more batteries 102 may be empty or essentially exhausted or otherwise unable to provide sufficient power to infuse liquid is approaching. In at least one embodiment, the continuous infusion time 191 of an infusion and the KVO time 192 may be displayed as a rate plot with the rate on the y-axis and time on the x-axis, for example.

By way of at least one embodiment, as the programmed infusion therapy progresses, by a given unit of time, for example number of minutes or hours, the completed fraction of the infusion phase may be grayed out on the leftmost portion of the bar graph 190 up to the current accumulated time 195 of the infusion phase. As such, in one or more embodiments, the user may easily observe that the elapsed infusion or therapy is quickly approaching the state when the one or more batteries 102 may be empty.

Figure 12:
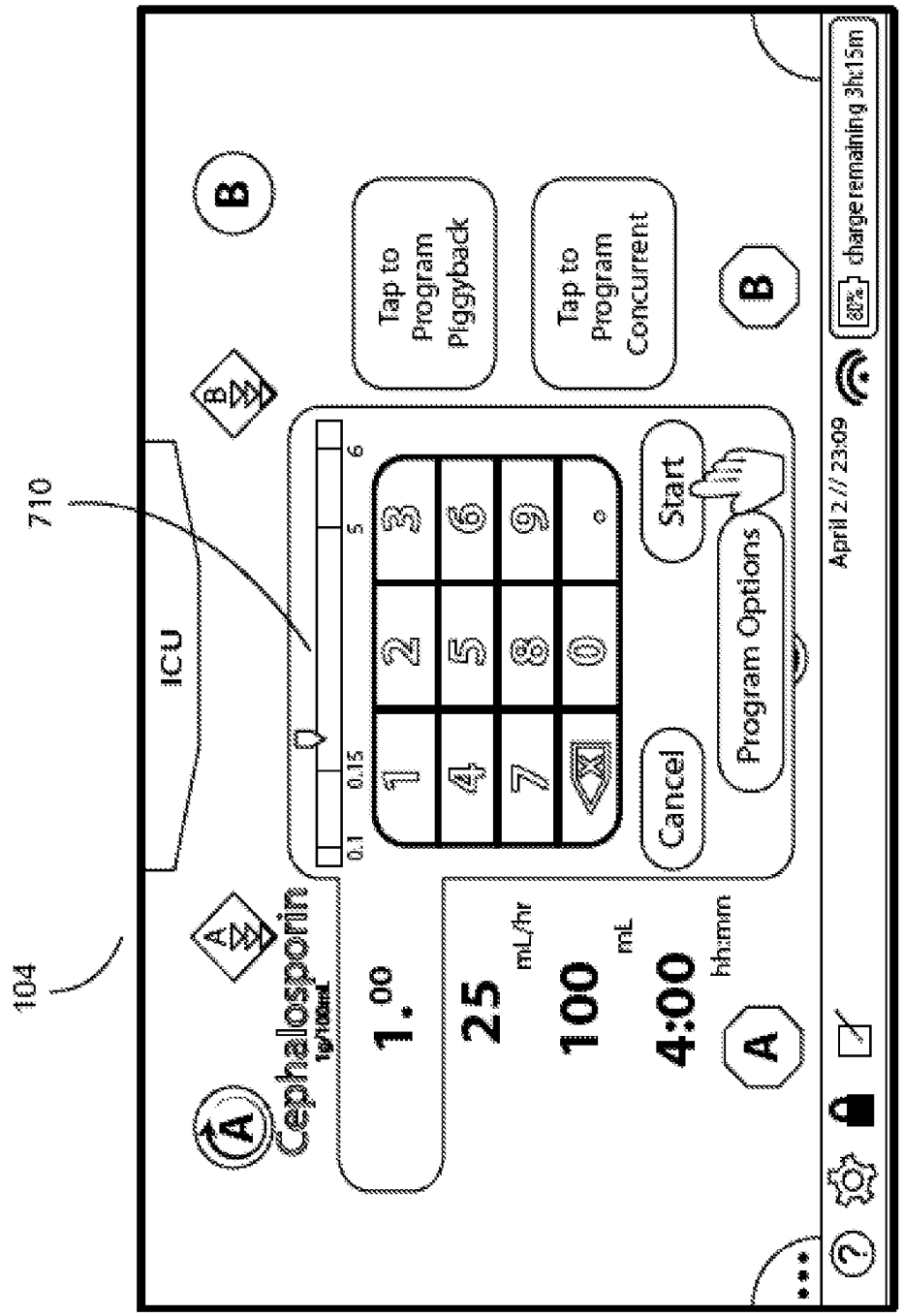
FIG. 12 shows an illustrative diagram of the infusion pump user interface screen displaying an option to change one or more requirements of the programmed infusion and remaining power capacity of one or more rechargeable batteries.

FIG. 12 shows an illustrative diagram of the infusion pump user interface screen displaying an option to change one or more requirements of the programmed infusion, according to one or more embodiments of the invention. In at least one embodiment, the energy requirements based on the programmed infusion parameters or requirements 140 may change over time. According to one or more embodiments, the parameters may change based on the process of ambulation or another scenario where main power is unavailable, and the battery 102 may deplete sooner than what the initial estimates had anticipated. For example, in at least one embodiment, such changes may be caused by one or more of extensive backlighting of the screen, touching the screen to check and monitor infusion parameters frequently, maintenance of a wireless connection that requires maximum power output from the receiver, and changes in delivery parameters.

In at least one embodiment of the invention, to minimize inaccuracies provided by the initial estimate, updates may be constantly performed by the infusion pump controller 105 based on energy requirement changes. For example, in one or more embodiments, if the charge estimate remaining falls by a predetermined amount, for example 10%, or below the time needed to fully execute the programmed therapy, when compared to the initial calculation, the one or more users may be informed with an alert message to deliver the updated information, via the user interface screen 104.

For example, by way of at least one embodiment, as shown in the Figures, the programmed infusion may require titration of the dose due to one or more varying needs or changes of the patient. In one or more embodiments, as one parameter or requirement of the plurality of requirements 140 may change, other requirements are changed or affected accordingly. In at least one embodiment, if the dose is decreased from 1.00 g/h to 0.20 g/h (as shown in FIG. 12), the remaining duration 150 of the programmed infusion will change from 1 hour to 5 hours. As such, in one or more embodiments, the estimated remaining battery charge is maintained, for example at 3 hours and 15 minutes, but the remaining battery charge may not be sufficient anymore to fully execute the programmed therapy for the new duration with the new infusion requirements.

As shown in FIG. 12, according to one or more embodiments, the one or more users (which may include the patient) may opt to titrate the dose for the current programmed infusion, wherein a hot titration dialog appears at the user interface screen 104, allowing the one or more users to enter a new dose. By way of at least one embodiment, the infusion pump controller 105 may determine, calculate and graphically display one or more changes 710 in one or more of the required remaining duration 150 of the programmed infusion to fully execute the programmed infusion, the anticipated power capacity requirement to execute the programmed infusion, and the remaining power capacity of the one or more rechargeable batteries 102.

For example, in at least one embodiment, the one or more users may reduce the dose from the originally programmed 1.00 g/h to 0.20 g/h. After the new parameter is entered via the user interface screen 104, depicted at 710, the one or more users may select "start" to titrate the therapy dose. In at least one embodiment, the change in the parameter requirements 140, such as the reduction in dose via titration, may result in an increased or decreased duration of therapy, such as from 1 hour to 5 hours, exceeding the estimated charge remaining of the one or more batteries 102 at 3 hours and 15 minutes. As such, in one or more embodiments, the infusion pump controller 105, via the user interface screen 104, may accentuate the battery charge indicator 160 and the estimated remaining duration to fully execute the current programmed infusion 150, and/or the one or more users may be alerted of the condition by audible means, such as a beep or a melody tone. In at least one embodiment of the invention, any other requirement of the plurality of infusion requirements 140 may be changed, in keeping with the invention.

Figure 13:
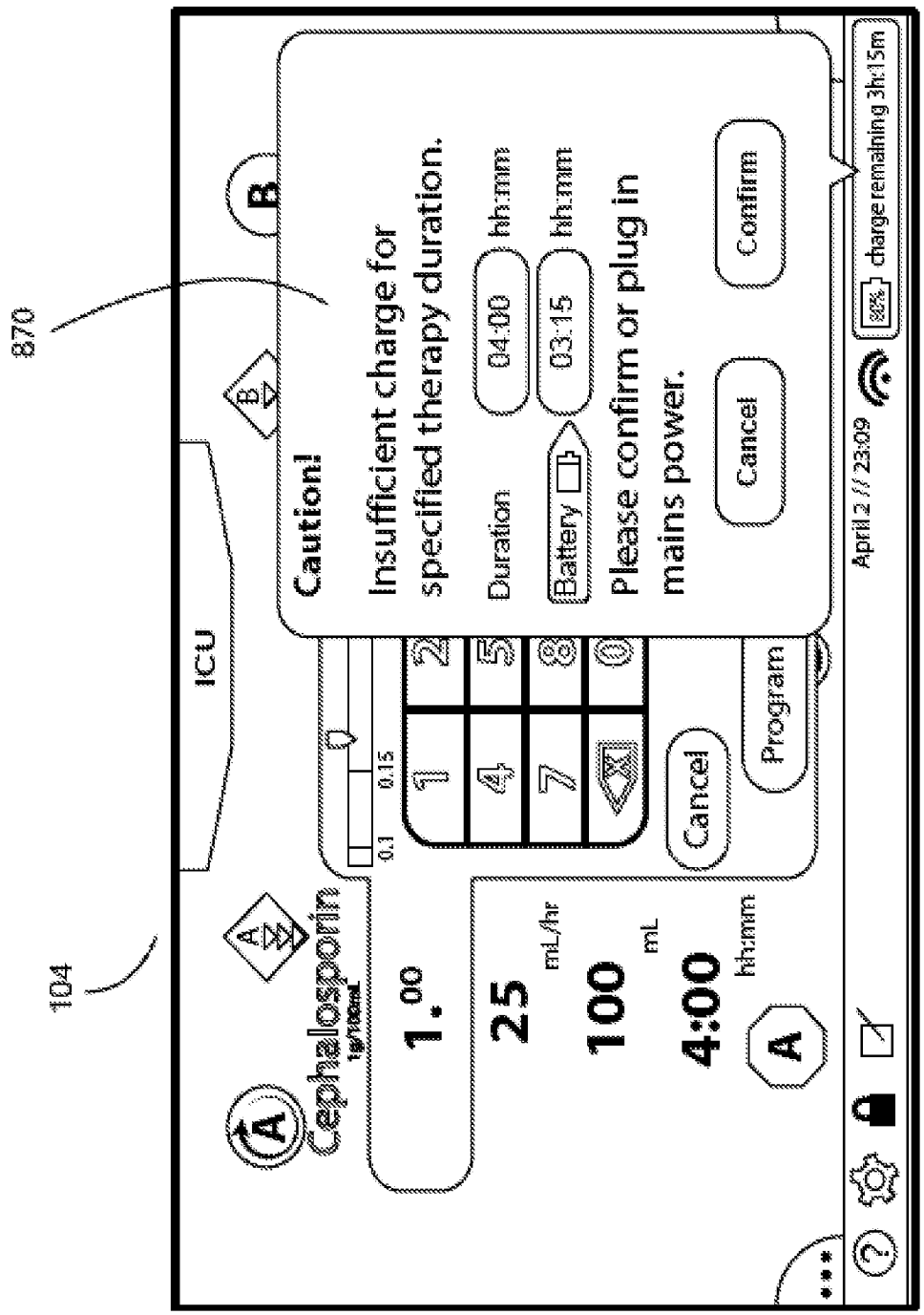
FIG. 13 shows an illustrative diagram of the infusion pump user interface screen displaying the remaining duration of a programmed infusion and the remaining power capacity of one or more rechargeable batteries after the one or more requirements of the programmed infusion are changed.

FIG. 13 shows an illustrative diagram of the infusion pump user interface screen 104 displaying the remaining duration of a programmed infusion and the remaining power capacity of one or more rechargeable batteries after the one or more requirements of the programmed infusion are changed, according to one or more embodiments of the invention. As shown in FIG. 13, in one or more embodiments, when the infusion pump controller 105 determines and calculates the one or more changes 710, the infusion pump controller 105 may provide an alert 870 to the one or more users, such as on the user interface screen 104, with updated information based on the determined and calculated one or more changes 710.

In one or more embodiments, the user interface screen 104 may display an additional confirmation screen or warning utilized to alert the one or more users of the change in remaining duration of the programmed infusion 150, and how the anticipated charge needed to fully execute the infusion therapy cannot be met on battery power alone. As such, in at least one embodiment, the one or more users may select to "confirm" the changes per dose titration, plug the infusion pump 101 into an AC power source or main power input, or cancel the titration or changes, via the user interface screen 104.

Figure 14:
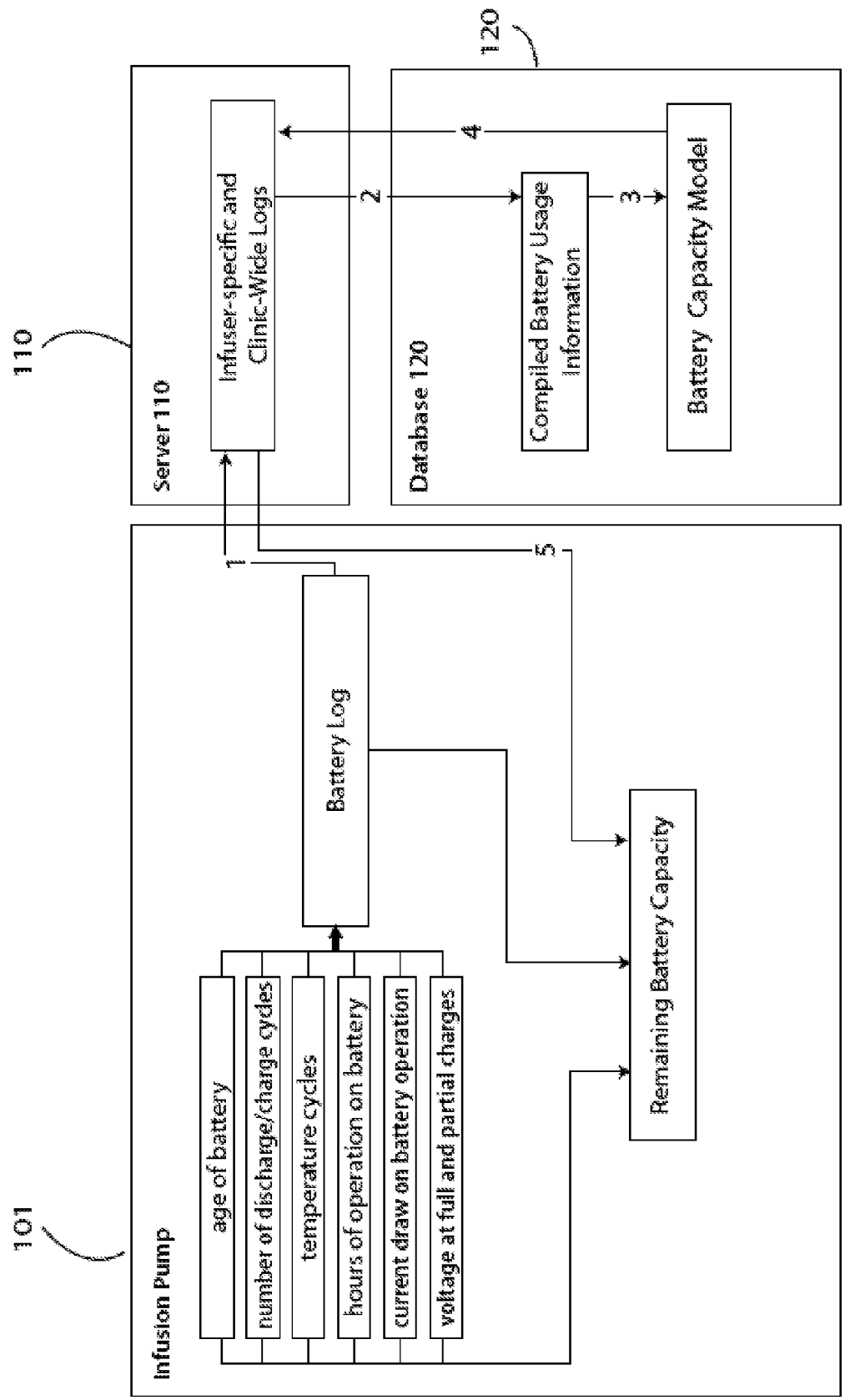
FIG. 14 shows an architectural view of an infusion pump battery charge alert system for logging battery usage and calculating battery capacity in communication with an external server and database that calculates and/or stores battery capacity models, according to one or more embodiments of the invention.

FIG. 14 shows an architectural view of an infusion pump battery charge alert system in communication with an external server and database, according to one or more embodiments of the invention. According to at least one embodiment of the invention, battery-related data such as usage, requirements and the calculated remaining power capacity of the one or more rechargeable batteries 102 may be continuously logged to a server 110 in order to define a battery capacity model of the one or more rechargeable batteries over time, such as in a database 120. In one or more embodiments of the invention, the usage and requirements of the one or more rechargeable batteries 102 may include one or more of age of the battery 102, number of discharge and charge cycles (complete and partial), temperature cycles experienced by the battery 102, hours of operation on battery power, current draw for battery powered operations, and voltage of the battery at full and partial charges. As shown in FIG. 14, according to at least one embodiment, the infusion pump may log the battery-related data throughout the infusion pump's 101 lifetime, wherein such information may be further compiled and analyzed to determine the useful capacity of the battery 102 as it ages with field use, and provide extensive data on real world usability.

In one or more embodiments, when the infusion pump 101 is directly or indirectly connected or networked to the server 110 and/or the database 120, the infusion pump 101 may be programmed to receive one or more of battery charge notification settings, drug library data, or other data as specified by an external institution, hospital, physician, etc. For example, according to at least one embodiment, a hospital may opt to enable ambulation detection and subsequent battery charge alerts for certain critical care conditions where ambulation is more prominent (such as in an ICU), while disabling or selecting lower priority alerts for other units (such as in pediatrics). In one or more embodiments, differentiations for battery charge alerts may be associated with certain drugs or fluids. For example, in at least one embodiment, aggressive alerts may be set for life-sustaining drugs or fluids.

By way of at least one embodiment, the battery log and the calculated remaining battery capacity may be transmitted to and from an external server 110, wherein routine log reporting via the server 110 may be utilized to model the expected capacity of the battery 102, such as by considering compiled data of a plurality of infusion pumps when compared to the infusion pump's 101 battery log, shown in FIG. 14. In one or more embodiments, the remaining battery capacity may be a function of battery-related parameters as well as the battery history, wherein estimation of remaining power capacity may be calculated by integrating current infusion-pump-specific parameters, as well as compiled battery usage information and the continuously developing battery capacity model. According to at least one embodiment of the invention, the remaining battery power capacity may be calculated as amount of charge still available to operate the infusion pump. In one or more embodiments, true residual battery capacity may be a complex function of battery temperature, age, and other parameters of the usage and requirements parameters discussed above. As shown in FIG. 14, in at least one embodiment of the invention, remaining battery power capacity estimation may consider the current battery voltage and current flux, and the historical and anticipated utilization. In at least one embodiment, the use of collective battery log data sets as described may be used to recursively refine the battery capacity model, enabling the infusion pump to provide a better estimate of the remaining charge. In one or more embodiments, as discussed above, the remaining capacity, such as mAh of charge remaining, may be used to estimate how long a programmed therapy may be sustained.

In one or more embodiments, during the charge or the recharge of the one or more rechargeable batteries 102, the infusion pump controller 105 may notify the one or more users when the remaining power capacity of the one or more batteries 102 is sufficient to fully execute the programmed infusion.

By way of one or more embodiments, in addition to or as an alternative to ambulation detection, the infusion pump battery charge alert system 100 may be utilized during a power outage or when a main power supply input becomes unavailable. In at least one embodiment, if an infusion therapy is started purely on battery power, an algorithm may be used to estimate the amount of time the infusion pump will remain active, and whether there is sufficient charge available to completely execute the programmed infusion. Using the algorithm, previous and current programming parameters and logged history of usage of the batteries 102 of the infusion pump 101, the infusion pump battery charge alert system 100 may prevent inadvertent, user-unanticipated stopping of therapy due to depletion of battery charge. In one or more embodiments, the algorithm utilized to estimate whether there is sufficient charge, divides the current capacity in ampere-hours by the current amperage drain of the apparatus, for example pump motor and current display drain to determine the amount of time remaining. In other embodiments, an average number of display related ampere-hour events expected, e.g., 4 per hour at K amps for 15 seconds each results in K ampere-minutes or K/60 ampere-hours where K depends on the type of display. The current capacity in ampere-hours is then divided by the sum of the current amperage drain added to the expected power use of the display, or K/60 for example. Any other algorithm that takes into account the battery age, type, history, temperature or any other value available to the system may also be utilized.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An infusion pump battery capacity management and battery charge alert system comprising:
    an infusion pump configured to infuse a fluid into a patient comprising
        one or more rechargeable batteries,
        a user interface and a user interface screen, and
        an infusion pump controller comprising a computer and coupled with said user interface and said user interface screen;
    wherein said infusion pump accepts an infusion input comprising a programmed infusion by one or more users via said user interface;
    wherein said user interface displays on said user interface screen a confirmation of said programmed infusion, and, a battery capacity assessment option;
    wherein said infusion pump controller accepts a selection input to select said battery capacity assessment option;
    wherein if said infusion pump controller detects said selection input associated with said battery capacity assessment option, said infusion pump controller
        calculates an anticipated power capacity requirement to execute said programmed infusion,
        calculates a remaining power capacity of said one or more rechargeable batteries,
        compares said calculated anticipated power capacity requirement to said calculated remaining power capacity of said one or more rechargeable batteries, and,
        determines whether said infusion pump is able to fully execute said programmed infusion based only on said remaining power capacity;
            wherein if said infusion pump controller determines wherein said infusion pump is able to fully execute said programmed infusion using only said remaining power capacity,
                said infusion pump controller executes said programmed infusion via said infusion pump only using said remaining power capacity; and
            wherein if said infusion pump controller determines wherein said infusion pump is unable to fully execute said programmed infusion only using said remaining power capacity, said infusion pump controller one or more of
                executes said programmed infusion via said infusion pump, and
                provides a message to said one or more users wherein a recharge time is required to fully execute said programmed infusion.

2. The infusion pump battery capacity management and battery charge alert system of claim 1, wherein said infusion pump controller
    accepts a selection input to select one or more of a program delay option and a start option, and asserts a respective option;
    wherein if said infusion pump controller detects said selection input associated with said start option,
        said programmed infusion is executed via said infusion pump;
    wherein if said infusion pump controller detects said selection input associated with said program delay option,
        an infusion delay is programmed and said infusion pump controller then selects said battery capacity assessment option or selects said start option.

3. The infusion pump battery capacity management and battery charge alert system of claim 1, wherein said user interface displays on said user interface screen
    a start screen with said confirmation of said programmed infusion,
    a start option,
    a battery charge indicator that indicates said remaining power capacity of said one or more rechargeable batteries as at least one of
        a percentage,
        a time,
    or both said percentage and said time; and,
    requirements of said programmed infusion.

4. The infusion pump battery capacity management and battery charge alert system of claim 1, wherein said notification includes
    wherein said remaining power capacity is insufficient to execute said programmed infusion,
    wherein a recharge time is required during execution of said programmed infusion, and
    a determination of a time before said one or more rechargeable batteries are depleted, or
    a determination of time before said one or more rechargeable batteries are depleted within a safety level.

5. The infusion pump battery capacity management and battery charge alert system of claim 1, wherein when said message is provided wherein a recharge time is required to fully execute said programmed infusion, said infusion pump is further configured to enter a first recharge state or a second recharge state,
    wherein said first recharge state includes a partial recharge of said one or more rechargeable batteries or a full recharge of said one or more rechargeable batteries, to fully execute said programmed infusion, and,
    wherein said second recharge state includes a full recharge of said one or more rechargeable batteries and a continuous recharge of said one or more rechargeable batteries during execution of said programmed infusion.

6. The infusion pump battery capacity management and battery charge alert system of claim 5, wherein during said first recharge state, said infusion pump controller is further configured to defer said partial or full recharge of said one or more rechargeable batteries via said one or more users, wherein said infusion pump is further configured to determine a time deferral value and notify said one or more users with said determined time deferral value, and, wherein said determined time deferral value is a value that allows said infusion pump to remain to operate safely before requiring said partial recharge or said fully recharge.

7. The infusion pump battery capacity management system and battery charge alert of claim 5, wherein during said second recharge state, said infusion pump controller is further configured to recharge said one or more rechargeable batteries by partially or fully recharging said one or more rechargeable batteries before execution of said programmed infusion and then continuously charging said one or more rechargeable batteries during execution of said programmed infusion, or partially or fully recharging said one or more rechargeable batteries during execution of said programmed infusion and continuously charging said one or more rechargeable batteries during execution of said programmed infusion, or deferring said recharge of said one or more rechargeable batteries, wherein said infusion pump is further configured to determine a time deferral value and notify said one or more users with said determined time deferral value, wherein said determined time deferral value is a value that allows said infusion pump to remain to operate safely before requiring said partial recharge or said fully recharge.

8. The infusion pump battery capacity management and battery charge alert system of claim 1, further comprising at least one detector that detects ambulation of said patient, wherein when said at least one detector detects patient ambulation, said infusion pump controller calculates and displays a required remaining duration of said programmed infusion to fully execute said programmed infusion, calculates the anticipated power capacity requirement to fully execute said programmed infusion, calculates the remaining power capacity of said one or more rechargeable batteries, compares said calculated anticipated power capacity requirement to said calculated remaining power capacity of said one or more rechargeable batteries, and, determines whether said infusion pump is able to fully execute said programmed infusion based on a comparison of said calculated required remaining duration of said programmed infusion and said calculated remaining power capacity of said one or more rechargeable batteries;

wherein when said infusion pump controller determines wherein said infusion pump is able to fully execute said programmed infusion with said required remaining duration of said programmed infusion using only said remaining power capacity, said infusion pump controller asserts said start option and said programmed infusion is executed via said infusion pump; and wherein when said infusion pump controller determines wherein said infusion pump is unable to fully execute said programmed infusion with said required remaining duration of said programmed infusion only using said remaining power capacity, said infusion pump controller provides a warning to said one or more users indicating insufficient remaining power capacity.

9. The infusion pump battery capacity management and battery charge alert system of claim 8, wherein said at least one detector that detects said ambulation of said patient comprises one or more of an accelerometer coupled with said computer wherein said accelerometer detects acceleration indicative of ambulation of said patient coupled with said infusion pump;

a wireless network interface coupled with said computer wherein said wireless interface detects wireless connectivity changes of said infusion pump coupled with said patient; and, a sensor that detects removal of a power input from said infusion pump.

10. The infusion pump battery capacity management and battery charge alert system of claim 9, wherein during said programmed infusion, said at least one detector detects ambulation based on removal of a power input from said infusion pump for less than a first predetermined value, and one or more of sustained infusion pump movements for at least a predetermined value of time detected by said accelerometer, and infusion pump movement based on a predetermined number of wireless connectivity changes detected by said wireless network interface.

11. The infusion pump battery capacity management and battery charge alert system of claim 8, wherein when said infusion pump controller determines wherein said infusion pump is unable to fully execute said programmed infusion with said required remaining duration of said programmed infusion only using said remaining power capacity, said infusion pump controller provides one or more of a duration of charge required of said one or more rechargeable batteries prior to starting the programmed infusion to fully execute said programmed infusion with said required remaining duration of said programmed infusion, and an anticipated time when a recharge of said one or more rechargeable batteries of said infusion pump is required during execution of said programmed infusion to fully execute said programmed infusion with said required remaining duration of said programmed infusion.

12. The infusion pump battery capacity management and battery charge alert system of claim 8, wherein said infusion pump displays on said user interface screen a time-remaining counter in hours and minutes that indicates said calculated required remaining duration of said programmed infusion to fully execute said programmed infusion.

13. The infusion pump battery capacity management and battery charge alert system of claim 8, wherein said infusion pump displays on said user interface screen a therapy-progress bar comprising said calculated required remaining duration of said programmed infusion to fully execute said programmed infusion;

said calculated remaining power capacity of said one or more rechargeable batteries; and a bar graph displaying a moving bar indicating the progress of said programmed infusion.

14. The infusion pump battery capacity management and battery charge alert system of claim 13, wherein said bar graph comprises a first segment displaying a first therapy option time of an infusion, a second segment displaying a second therapy option time of an infusion, wherein said first therapy option time of an infusion and said second therapy option time are displayed as a rate plot, a third segment highlighted alone one or more of said first segment and said second segment that indicates when said remaining power capacity of said one or more rechargeable batteries will be essentially exhausted.

15. The infusion pump battery capacity management and battery charge alert system of claim 8, wherein said infusion pump controller determines and calculates one or more changes in said required remaining duration of said programmed infusion to fully execute said programmed infusion, said anticipated power capacity requirement to execute said programmed infusion, and, said remaining power capacity of said one or more rechargeable batteries.

\* \* \* \* \*